United States Patent
Watanabe et al.

(10) Patent No.: US 10,974,246 B2
(45) Date of Patent: Apr. 13, 2021

(54) HIGH-DENSITY MICRO-CHAMBER ARRAY AND MEASUREMENT METHOD USING SAME

(71) Applicant: JAPAN SCIENCE AND TECHNOLOGY AGENCY, Kawaguchi (JP)

(72) Inventors: Rikiya Watanabe, Tokyo (JP); Hiroyuki Noji, Tokyo (JP); Naoki Soga, Tokyo (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 581 days.

(21) Appl. No.: 15/567,431

(22) PCT Filed: Jun. 7, 2016

(86) PCT No.: PCT/JP2016/066834
§ 371 (c)(1),
(2) Date: Oct. 18, 2017

(87) PCT Pub. No.: WO2016/199741
PCT Pub. Date: Dec. 15, 2016

(65) Prior Publication Data
US 2018/0104686 A1   Apr. 19, 2018

(30) Foreign Application Priority Data

Jun. 8, 2015   (JP) .............................. JP2015-116045

(51) Int. Cl.
*B01L 3/00*   (2006.01)
*C12M 1/00*   (2006.01)
(Continued)

(52) U.S. Cl.
CPC .......... *B01L 3/5085* (2013.01); *B01J 19/0046* (2013.01); *C12M 1/00* (2013.01);
(Continued)

(58) Field of Classification Search
CPC ........... B01L 3/5085; B01L 2300/0877; B01L 2200/142; B01L 2200/0642;
(Continued)

(56) References Cited

U.S. PATENT DOCUMENTS

| 6,124,138 A | 9/2000 | Woudenberg et al. |
| 2004/0013654 A1 | 1/2004 | Kramer et al. |

(Continued)

FOREIGN PATENT DOCUMENTS

| CN | 101203748 A | 6/2008 |
| CN | 101932933 A | 12/2010 |

(Continued)

OTHER PUBLICATIONS

China National Intellectual Property Administration, "First Office Action," issued in CN Patent Application No. 201680033367.0, which is a Chinese counterpart of U.S. Appl. No. 15/567,431, dated Aug. 7, 2019, 14 pages (11 pages of original Chinese Office Action and 3 pages of English translation of Chinese Office Action).

(Continued)

*Primary Examiner* — Samuel P Siefke
*Assistant Examiner* — Quocan B Vo

(57) ABSTRACT

A high-density micro-chamber array has a translucent flat substrate, a hydrophobic layer in which a plurality of micro-chambers are provided, and a lipid bilayer membrane formed in each of the openings of the micro-chambers, wherein an electrode is provided in each of the micro-chambers, and when the side of the substrate on which the hydrophobic layer is provided is directed upward, the micro-chamber array is configured such that with at least one of the (Continued)

following A) and B) being met, light entering the substrate from below is transmitted through the substrate and penetrates into the micro-chambers' interiors, and light entering the substrate from the micro-chambers' interiors is transmitted through the substrate and escapes toward below the substrate. A) The electrode is provided on an inner side surface of each of the micro-chambers. B) The electrode is transparent and provided on a bottom surface of each of the micro-chambers.

11 Claims, 17 Drawing Sheets

(51) Int. Cl.
*G01N 33/48* (2006.01)
*B01J 19/00* (2006.01)
*G01N 33/487* (2006.01)

(52) U.S. Cl.
CPC ....... *G01N 33/48* (2013.01); *G01N 33/48707* (2013.01); *B01J 2219/00317* (2013.01); *B01J 2219/00331* (2013.01); *B01J 2219/00619* (2013.01); *B01J 2219/00621* (2013.01); *B01J 2219/00653* (2013.01); *B01J 2219/00702* (2013.01); *B01J 2219/00725* (2013.01); *B01J 2219/00734* (2013.01); *B01L 2200/0642* (2013.01); *B01L 2200/0647* (2013.01); *B01L 2200/0689* (2013.01); *B01L 2200/12* (2013.01); *B01L 2200/142* (2013.01); *B01L 2300/0645* (2013.01); *B01L 2300/0819* (2013.01); *B01L 2300/0861* (2013.01); *B01L 2300/0877* (2013.01); *B01L 2300/165* (2013.01)

(58) Field of Classification Search
CPC ......... B01L 2300/0645; B01L 2200/12; B01L 2300/0819; B01L 2300/0861; B01L 2300/165; C12M 1/00; G01N 33/48; G01N 33/48707; B01J 19/0046; B01J 2219/00653; B01J 2219/00702; B01J 2219/00619; B01J 2219/00621; B01J 2219/00734; B01J 2200/0647; B01J 2219/00317; B01J 2219/00331; B01J 2219/00725; B01J 2200/0689

See application file for complete search history.

(56) References Cited

U.S. PATENT DOCUMENTS

| | | |
|---|---|---|
| 2006/0029955 A1* | 2/2006 | Guia ................. B65B 31/00 435/6.11 |
| 2009/0101499 A1 | 4/2009 | Katsuki et al. |
| 2009/0167288 A1 | 7/2009 | Reid et al. |
| 2010/0092341 A1 | 4/2010 | Hummel et al. |
| 2010/0156444 A1* | 6/2010 | Ponjee ............. B01L 3/5027 324/703 |
| 2011/0120871 A1 | 5/2011 | Reid et al. |
| 2013/0118905 A1* | 5/2013 | Morimoto ......... B01L 3/502761 204/643 |
| 2013/0136863 A1 | 5/2013 | Hiyama et al. |
| 2014/0054170 A1 | 2/2014 | Tsukahara et al. |
| 2014/0134711 A1 | 5/2014 | Boese |
| 2016/0296928 A1 | 10/2016 | Noji et al. |

FOREIGN PATENT DOCUMENTS

| | | |
|---|---|---|
| CN | 103180735 A | 6/2013 |
| CN | 103502805 A | 1/2014 |
| JP | 2004-520816 A | 7/2004 |
| JP | 2009-025313 A | 2/2009 |
| JP | 2011-506994 A | 3/2011 |
| JP | 2011-147409 A | 8/2011 |
| JP | 2013-126381 A | 6/2013 |
| JP | 2014-021025 A | 2/2014 |
| JP | 2014-178121 A | 9/2014 |
| JP | 2015-040754 A | 3/2015 |
| WO | 2009/077734 A2 | 6/2009 |
| WO | 2015/025822 A1 | 2/2015 |

OTHER PUBLICATIONS

International Search Report received for PCT Patent Application No. PCT/JP2016/066834 dated Aug. 30, 2016, 5 pages (2 pages of English translation of International Search Report, and 3 pages of International Search Report).

Japan Patent Office, "Notice of Reasons for Refusal," issued in Japanese Patent Application No. 2017-523637, which is a Japanese counterpart of U.S. Appl. No. 15/567,431, dated Apr. 23, 2019, 10 pages.

European Patent Office, "Extended European Search Report," issued in European Patent Application No. 16 807 448.2, which is a European counterpart of U.S. Appl. No. 15/567,431, dated Jun. 17, 2019, 9 pages.

\* cited by examiner

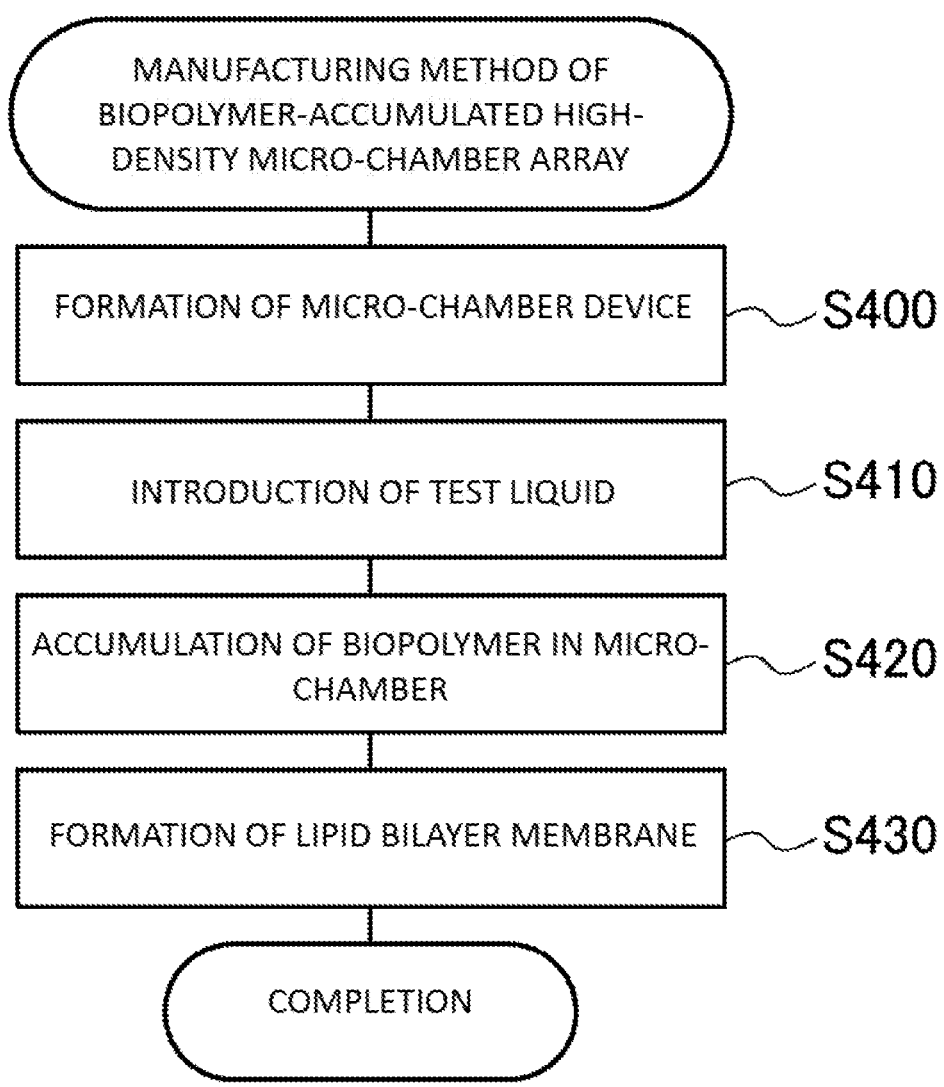

HIGH-DENSITY MICRO-CHAMBER ARRAY AND MEASUREMENT METHOD USING SAME

CROSS REFERENCE TO RELATED APPLICATIONS

This patent application is a U.S. national stage application under 35 U.S.C. § 371 of International Patent Application No. PCT/JP2016/066834 filed on Jun. 7, 2016, which claims the benefit of foreign priority to Japanese Patent Application No. JP 2015-116045 filed on Jun. 8, 2015. The International Application was published in Japanese on Dec. 15, 2016, as International Publication No. WO 2016/199741 A1 under PCT Article 21(2).

TECHNICAL FIELD

The present invention relates to a high-density micro-chamber array, and a measurement method using same.

BACKGROUND ART

Patent Literature 1 discloses a high-density micro-chamber array which has a flat substrate, a plurality of micro-chambers being formed in a hydrophobic substance on the surface of the substrate in such a way as to be arrayed regularly at a high density and each having a capacity of $4,000\times10^{-18}$ m$^3$ or smaller, and a lipid bilayer membrane being formed in such a way as to liquid-seal an aqueous test solution in each opening of the plurality of micro-chambers in the state of being filled with the aqueous test solution.

CITATION LIST

Patent Literature

Patent Literature 1: Japanese Patent Laid-Open No. 2015-040754

SUMMARY OF INVENTION

Technical Problem

Based on the above conventional high-density micro-chamber array, the development of its application technology has been demanded.

Solution to Problem

A high-density micro-chamber array according to a first aspect has a translucent flat substrate, a hydrophobic layer provided on the substrate and composed of a hydrophobic substance wherein on the principal surface of the hydrophobic layer, openings of a plurality of micro-chambers, each having a capacity of $4,000\times10^{-18}$ m$^3$ or smaller, are provided in such a way as to be arrayed regularly at a high density, and a lipid bilayer membrane formed, in such a way as to seal a test liquid, in each of the openings of the plurality of micro-chambers in the state of being filled with the test liquid, wherein an electrode is provided in each of the micro-chambers; and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate.

A) The electrode is provided on an inner side surface of each of the micro-chambers.

B) The electrode is provided as a transparent electrode on a bottom surface of each of the micro-chambers.

An analysis method of a membrane protein according to a second aspect involves: providing a high-density micro-chamber array which has a translucent flat substrate, and a hydrophobic layer provided on the substrate and composed of a hydrophobic substance wherein on the principal surface of the hydrophobic layer, openings of a plurality of micro-chambers, each having a capacity of $4,000\times10^{-18}$ m$^3$ or smaller, are provided in such a way as to be arrayed regularly at a high density, wherein an electrode is provided in each of the micro-chambers, and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate; forming a lipid bilayer membrane in each of the openings of the plurality of micro-chambers, wherein the lipid bilayer membrane is to hold the membrane protein; and applying a voltage between the electrode and a counter electrode provided above the lipid bilayer membrane to thereby change the properties of the membrane protein.

A) The electrode is provided on an inner side surface of each of the micro-chambers.

B) The electrode is provided as a transparent electrode on a bottom surface of each of the micro-chambers.

A method according to a third aspect involves: providing a high-density micro-chamber array which has a translucent flat substrate, and a hydrophobic layer provided on the substrate and composed of a hydrophobic substance wherein on the principal surface of the hydrophobic layer, openings of a plurality of micro-chambers, each having a capacity of $4,000\times10^{-18}$ m$^3$ or smaller, are provided in such a way as to be arrayed regularly at a high density, wherein an electrode is provided in each of the micro-chambers, and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate; applying a voltage to the electrode to accumulate a biopolymer in the interiors of the plurality of micro-chambers; and thereafter forming a lipid bilayer membrane in each of the openings of the plurality of micro-chambers in such a way as to seal the biopolymer.

A) The electrode is provided on an inner side surface of each of the micro-chambers.

B) The electrode is provided as a transparent electrode on a bottom surface of each of the micro-chambers.

Advantageous Effects of Invention

Application technologies of a high-density micro-chamber array are provided.

BRIEF DESCRIPTION OF DRAWINGS

FIG. 15 is a process diagram showing one example of a manufacturing method of the biopolymer-accumulated high-density micro-chamber array in the third embodiment.

DESCRIPTION OF EMBODIMENTS

Figure 1:
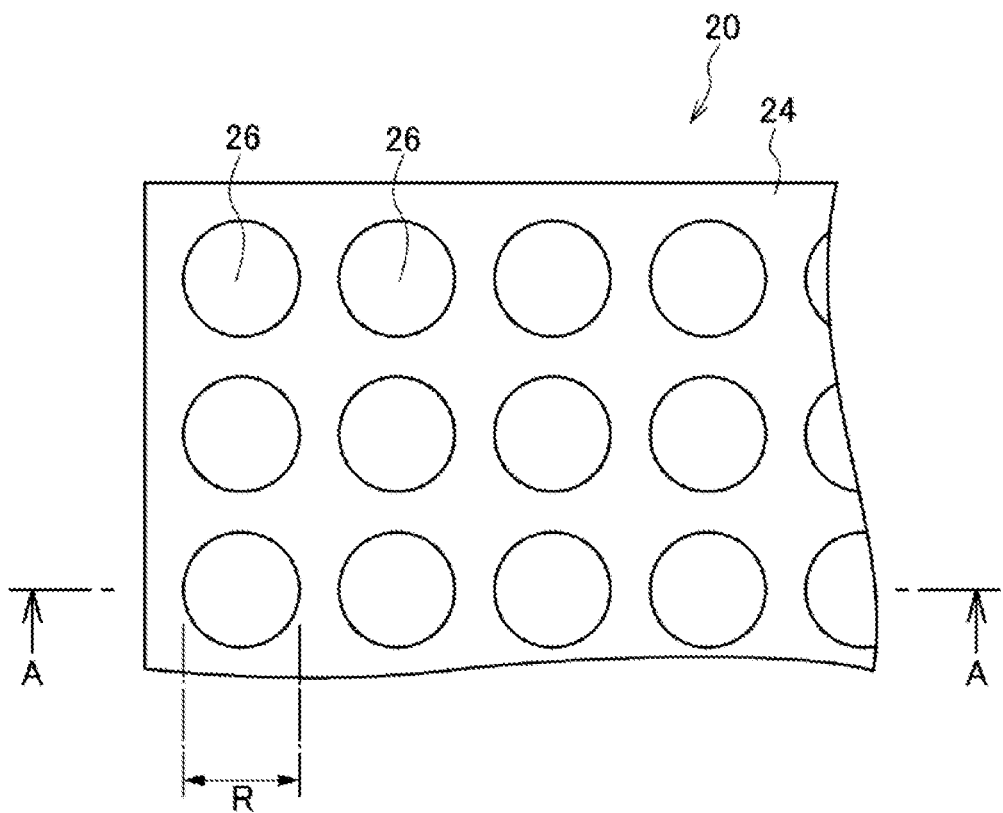
FIG. 1 is a plan view illustrating one example of a schematic configuration of a high-density micro-chamber array according to a first embodiment.

In various types of biomolecular reactions caused through lipid bilayer membranes, for example, the membrane transport process, the membrane permeation reactions and enzymatic reactions on the membrane surfaces, since the diffusion of reaction products take long times and changes in the substance concentrations along with enzymatic activities are remarkably mild, and so on, it is liable to become difficult to detect various types of biomolecular reactions caused through lipid bilayer membranes with a high sensitivity. When the capacity of chambers is large, the concentration change in the chambers becomes small and the detection as a concentration change becomes difficult. When the number of chambers is small, since the reaction of biomolecules is very slow, there arises the case where the reaction is not caused in all the chambers and the detection becomes difficult. Therefore, a high-density micro-chamber array is demanded in which a large number of micro-chambers liquid-sealed with lipid bilayer membranes and having a very small capacity are formed at a high density. Patent Literature 1 discloses such a high-density micro-chamber array. The application technologies thereof have, however, unstudied fields.

The present inventors have studied exhaustively to find application technologies of the conventional high-density micro-chamber array. As a result, the present inventors have gained the following finding. Here, the following finding has become a clue to achievement of the present invention, and does not limit the present invention.

That is, the development of the above high-density micro-chamber array has enabled measurements of the transmembrane-type substance transport and the like by membrane proteins to be efficiently carried out. By the way, there is the case where the activity of the membrane proteins is affected by the membrane potential. In vivo, there is also the case where the membrane potential is positively controlled by the active transport of ions and the activity of the membrane proteins is thereby regulated. If the membrane potential can be controlled in lipid bilayer membranes formed in the high-density micro-chamber array, the properties of the membrane proteins may possibly be elucidated in more detail. In the conventional high-density micro-chamber array, however, the membrane potential cannot be controlled.

Based on such an insight, the present inventors have thought that in the conventional high-density micro-chamber array, forming an electrode in the chamber interior enables the membrane potential of the lipid bilayer membranes to be controlled. Controlling the membrane potential by using the electrode enables measuring how the properties of membrane proteins vary according to the membrane potential.

Providing the electrode in the chamber interior has resulted in exploiting further application aspects of the conventional high-density micro-chamber array. That is, generating heat by applying a current to the electrode enables the temperature of the chamber to be controlled. Generating an electric field by using the electrode enables biopolymers and the like to be induced and accumulated in the chamber interior. In order to transfer membrane proteins on the cell surfaces to lipid bilayer membranes spread on the chambers, technologies of cell fusion is allowed to be used.

The substrate and the like are configured to have translucency. By making such a configuration that light entering the substrate from below the substrate is transmitted through the substrate and penetrates into the interiors of the micro-chambers, and light entering the substrate from the interiors of the micro-chambers is transmitted through the substrate and escapes toward below the substrate, the reaction in micro-chambers can be effectively detected.

Hereinafter, embodiments of the present invention will be described by reference to the attached drawings. Here, the following embodiments are strictly examples, and do not limit the present invention.

Any of the embodiments to be described hereinafter shows a desirable specific example of the present invention. Numerical values, shapes, materials, constituents, arranging positions and connecting forms of the constituents, steps, orders of steps, and the like, indicated in the following embodiments, are strictly examples, and do not limit the present invention. Further among the constituents in the following embodiments, constituents not described in independent claims, indicating the most significant concepts of the present invention, will be interpreted as optional constituents constituting more desirable forms. Further in the drawings, for constituents having the same reference sign, the description will be omitted in some cases. Further in order to facilitate understanding the drawings, each of the constituents is schematically illustrated, and shapes, dimensions and the like are not exactly indicated in some cases. Further in the manufacturing method, as required, the order and the like of steps may be altered and other steps may be added.

First Embodiment

A high-density micro-chamber array according to a first embodiment has a translucent flat substrate, a hydrophobic layer provided on the substrate and composed of a hydrophobic substance wherein on the principal surface of the hydrophobic layer, openings of a plurality of micro-chambers, each having a capacity of $4,000 \times 10^{-18}$ m$^3$ or smaller, are provided in such a way as to be arrayed regularly at a high density, and a lipid bilayer membrane formed, in such a way as to seal a test liquid, in each of the openings of the plurality of micro-chambers in the state of being filled with the test liquid, wherein an electrode is provided in each of the micro-chambers; and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate.

A) The electrode is provided on an inner side surface of each of the micro-chambers.

B) The electrode is provided as a transparent electrode on a bottom surface of each of the micro-chambers.

The above high-density micro-chamber array may further have a counter electrode above the lipid bilayer membranes.

The above high-density micro-chamber array may further have a liquid channel having a bottom surface formed by a surface on which the micro-chambers are formed.

The above liquid channel may be formed between the upper surface of the hydrophobic layer and the lower surface of a ceiling disposed above the hydrophobic layer. The ceiling may be constituted of a glass plate.

A high-density micro-chamber array system according to the first embodiment has the above high-density micro-chamber array, and a voltage-applying apparatus to apply a voltage between the electrode and the counter electrode.

An analysis method of a membrane protein according to the first embodiment involves: providing a high-density micro-chamber array which has a translucent flat substrate, and a hydrophobic layer provided on the substrate and composed of a hydrophobic substance wherein on the principal surface of the hydrophobic layer, openings of a plurality of micro-chambers, each having a capacity of $4,000 \times 10^{-18}$ m$^3$ or smaller, are provided in such a way as to be arrayed regularly at a high density, wherein an electrode is provided in each of the micro-chambers, and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate; forming a lipid bilayer membrane in each of the openings of the plurality of micro-chambers, wherein the lipid bilayer membrane is to hold the membrane protein; and applying a voltage between the electrode and a counter electrode provided above the lipid bilayer membrane to thereby change the properties of the membrane protein.

A) The electrode is provided on an inner side surface of each of the micro-chambers.

B) The electrode is provided as a transparent electrode on a bottom surface of each of the micro-chambers.

[Apparatus Configuration]

Figure 2:
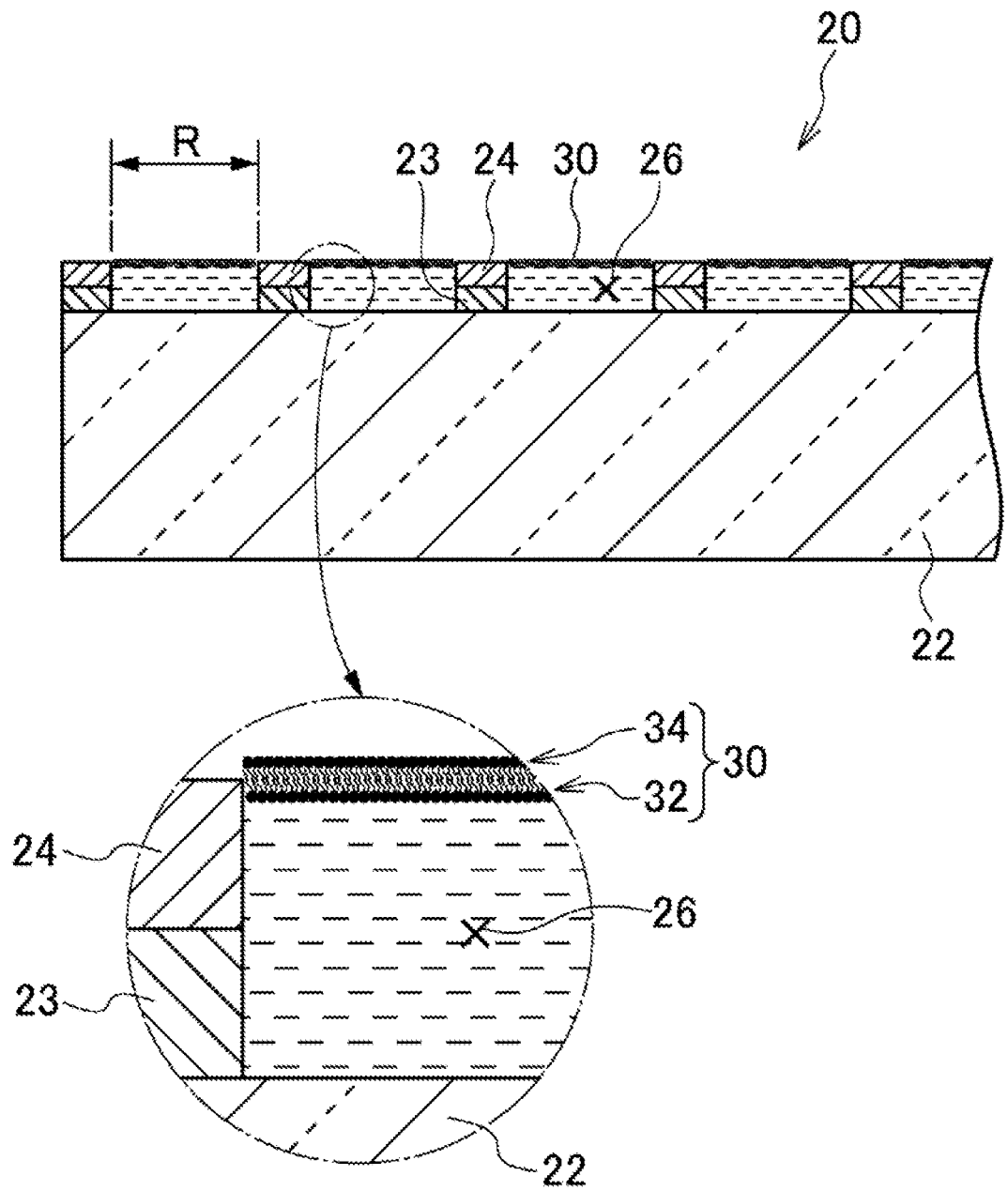
FIG. 2 is a view of an A-A cross-section in FIG. 1 of the high-density micro-chamber array according to the first embodiment, and an enlarged view of part of the cross-section.

FIG. 1 is a plan view illustrating one example of a schematic configuration of a high-density micro-chamber array according to the first embodiment. FIG. 2 is a view of an A-A cross-section in FIG. 1 of the high-density micro-chamber array according to the first embodiment, and an enlarged view of part of the cross-section. Hereinafter, by reference to FIG. 1 and FIG. 2, an apparatus configuration of a high-density micro-chamber array 20 of the first embodiment will be described.

As illustrated in FIG. 1 and FIG. 2, the high-density micro-chamber array 20 has a substrate 22, a hydrophobic layer 24, lipid bilayer membranes 30 and electrodes 23.

The substrate 22 has translucency, and is flat. The substrate 22 can be constituted of, for example, a glass or an acrylic resin. The material, the thickness, the shape and the like of the substrate 22 are not especially limited as long as light entering the substrate 22 from below the substrate 22 can be transmitted through the substrate 22 and penetrate into the interiors of micro-chambers 26, and light entering the substrate 22 from the interiors of the micro-chambers 26 can be transmitted through the substrate 22 and escape toward below the substrate 22. Specifically, for example, the thickness may be 0.1 mm or larger and 5 mm or smaller, or 0.3 mm or larger and 3 mm or smaller, or 0.7 mm or larger and 1.5 mm or smaller. The size of the substrate 22 in plan view is not especially limited.

The hydrophobic layer 24 is a layer provided on the substrate 22 and composed of a hydrophobic substance. The hydrophobic substance includes, for example, hydrophobic resins such as fluororesins, and substances other than resins, such as glass. The thickness of the hydrophobic layer 24 can suitably be regulated according to the capacity of micro-chambers described later. Specifically, for example, the thickness may be 10 nm or larger and 100 µm or smaller, or 100 nm or larger and 5 µm or smaller, or 250 nm or larger and 1 µm or smaller.

On the hydrophobic layer 24, openings of a plurality of micro-chambers 26 are provided in such a way as to be arrayed regularly and at a high density on the principal surface of the hydrophobic layer 24. The capacity of the micro-chamber 26 is $4,000 \times 10^{-18}$ m$^3$ or smaller ($4,000$ µm$^3$ or smaller). The capacity of the micro-chamber 26 may be, for example, $0.1 \times 10^{-18}$ m$^3$ or larger and $4,000 \times 10^{-18}$ m$^3$ or smaller, or $0.5 \times 10^{-18}$ m$^3$ or larger and $400 \times 10^{-18}$ m$^3$ or smaller, or $1 \times 10^{-18}$ m$^3$ or larger and $40 \times 10^{-18}$ m$^3$ or smaller.

As illustrated in FIG. 1 and FIG. 2, the micro-chambers 26 may assume a cylindrical shape. As illustrated in FIG. 1 and FIG. 2, the micro-chambers 26 may assume a cylindrical shape in which the substrate 22 provides the bottom surface of the micro-chambers 26 and the hydrophobic layer 24 (or the hydrophobic layer 24 and the electrode 23) provides the side surface thereof.

Since the capacity of the micro-chamber 26 is made to be $4,000 \times 10^{-18}$ m$^3$ or smaller, by using the high-density micro-chamber array 20 of the first embodiment for detection of a biomolecular reaction, the number of biomolecules in the micro-chamber 26 can be reduced. Consequently, the concentration change in the chamber by the reaction of one biomolecule can be made large and the detection sensitivity in detection as a concentration change can be made high; so, even if the biomolecular reaction is remarkably slow, the biomolecular reaction can be detected at a high sensitivity. Further since the configuration is made in such a way as to have the array in which such minute micro-chambers 26 are formed at a high density in large numbers, even if the frequency of occurrence of the biomolecular reaction is low, the reaction occurs in some of the chambers; therefore, the biomolecular reaction can be detected at a high sensitivity. Here, the capacity of the micro-chamber 26 is to be determined according to the magnitude of the reaction rate of a biomolecule as a test object, the content of the biomolecule, and the like; and for the case where the reaction rate of the biomolecule is high, the capacity is suitably made to be $4,000 \times 10^{-18}$ m$^3$ or smaller, and for the case where the magnitude of the reaction rate of the biomolecule is low, and so on, the capacity may be made to be $1,000 \times 10^{-18}$ m$^3$ or smaller or $100 \times 10^{-18}$ m$^3$ or smaller.

The depth of the micro-chamber 26 may be, for example, 10 nm or larger and 100 µm or smaller, or 100 nm or larger and 5 µm or smaller, or 250 nm or larger and 1 µm or smaller.

The opening of the micro-chamber 26 can be made to be, for example, circular. The diameter of a circle in the case of being made to be circular may be, for example, 0.1 µm or larger and 100 µm or smaller, or 0.5 µm or larger and 50 µm or smaller, or 1 µm or larger and 10 µm or smaller.

"Regularly" refers to the arrangement of the chambers, for example, as viewed in the thickness direction of the substrate, in a lattice form, a matrix form, zigzags or the like on the substrate. "Regularly" can mean that, for example, the chambers are arrayed at certain intervals in such a way as to form a plurality of rows.

"A high density" means that the number of chambers per square mm (mm) may be $0.1 \times 10^3$ or larger and $2,000 \times 10^3$ or smaller, or $1 \times 10^3$ or larger and $1,000 \times 10^3$ or smaller, or $5 \times 10^3$ or larger and $100 \times 10^3$ or smaller. In terms of per cm$^2$ ($1 \times 10^{-4}$ [m$^2$]), the number may be $10 \times 10^3$ or larger and $200 \times 10^6$ or smaller, or $100 \times 10^3$ or larger and $100 \times 10^6$ or smaller, or $0.5 \times 10^6$ or larger and $10 \times 10^6$ or smaller.

In the high-density micro-chamber array 20, the plurality of micro-chambers 26 can also be ones which are formed in such a way as to have a depth of 100 m or smaller, and an equivalent-circle diameter of 100 m or smaller, ones which are formed in such a way as to have a depth of 2 µm or smaller, and an equivalent-circle diameter of 10 µm or smaller, or ones which are formed in such a way as to have a depth of 1 µm or smaller, and an equivalent-circle diameter of 5 µm or smaller. In this configuration, the high-density micro-chamber array 20 can be formed by using means of forming a thin film composed of a hydrophobic substance and an electrode layer on the surface of the substrate 22, and forming the plurality of micro-chambers 26 on the thin film, and can relatively easily be formed.

The micro-chambers 26 can also be ones which are formed in such a way as to have an equivalent-circle diameter in a predetermined diameter range including 1 µm on the thin film composed of the hydrophobic substance and the electrode layer each having a thickness in a predetermined thickness range including 500 nm. In consideration of the magnitude of the reaction rate of a biomolecule as a test object and the content of the biomolecule, and also in consideration of easiness of their manufacture, it is conceivably suitable that the depth and the diameter of the micro-chambers 26 are several hundred nanometers to several micrometers. Here, "a predetermined thickness range" can be made, for example, to be a range of 50 nm, being 0.1 time 500 nm, or larger and 5 µm, being 10 times 500 nm, or smaller, or to be a range of 250 nm, being 0.5 time 500 nm, or larger and 1 µm, being 2 times 500 nm, or smaller. "A predetermined diameter range" can be made, for example, to be a range of 100 nm, being 0.1 time 1 µm, or larger and 10 µm, being 10 times 1 µm, or smaller, or to be a range of 500 nm, being 0.5 time 1 µm, or larger and 2 µm, being 2 times 1 µm, or smaller.

The "predetermined thickness range" is not especially limited. The thickness may be, for example, 10 nm or larger and 500 nm or smaller, or 20 nm or larger and 500 nm or smaller, or 30 nm or larger and 500 nm or smaller. The "predetermined thickness range" may be, for example, 10 nm or larger and 100 nm or smaller, or 20 nm or larger and 100 nm or smaller, or 30 nm or larger and 100 nm or smaller. When the depth of the micro-chambers is made small (several tens of nanometers) and the capacity thereof is made small (about several hundred attoliters), the measurement sensitivity is further improved (Soga, N., et al., 2015, Attolitre-sized lipid bilayer chamber array for rapid detection of single transporters, Scientific Reports, 5:11025).

In one example, each micro-chamber 26 is formed in a hydrophobic layer 24 and an electrode 23 having a thickness D of 1 μm in such a way as to have a diameter R of 5 μm. Therefore, the capacity L of each of the micro-chambers 26 is L=π$(2.5 \times 10^{-6})^2 \times 1 \times 10^{-6}$ [m³]≈$19.6 \times 10^{-18}$ [m³]. When micro-chambers 26 are tentatively arrayed at intervals of 2 μm in length and breadth, the area S necessary for one micro-chamber 26 becomes that of a square of 7 μm in one side, and calculated as S=$(7 \times 10^{-6})^2$ [m²]=$49 \times 10^{-12}$ [m²]. Therefore, on a glass substrate 22, micro-chambers 26 of about $2 \times 10^6$ in number per cm² ($1 \times 10^{-4}$ [m²]) ($20 \times 10^3$ per square mm) are resultantly formed.

A lipid bilayer membrane 30 is formed, in such a way as to seal a test liquid, on each opening of the plurality of micro-chambers 26 in the state of being filled with the test liquid. The test liquid is not especially limited as long as being a liquid capable of forming the lipid bilayer membrane 30, but can specifically be made to be, for example, an aqueous solution.

The lipid bilayer membrane 30 is formed such that a first lipid membrane 32 in which hydrophilic groups of a lipid directed to the micro-chamber 26 side (in FIG. 2, downward) and a second lipid membrane 34 in which hydrophobic groups of a lipid directed to the micro-chamber 26 side (in FIG. 2, downward) are stacked so that their hydrophobic groups are inside. As the lipids constituting the first lipid membrane 32 and the second lipid membrane 34, there can be used natural lipids derived from soybeans, *Bacillus coli* and the like, and artificial lipids such as DOPE (dioleoylphosphatidylethanolamine) and DOPG (dioleoylphosphatidylglycerol).

The lipid bilayer membrane 30 can also be made to be one in which a membrane protein is reconstituted. In this configuration, the high-density micro-chamber array 20 can be used for the detection of biomolecular reactions through various types of membrane proteins. A method of reconstitution of a membrane protein in the lipid bilayer membrane 30 will be described later.

The electrode 23 is provided inside each of the micro-chambers 26. The electrodes 23 may each be mutually electrically connected. In the substrate 22, when the side thereof on which the hydrophobic layer 24 is provided is directed upward, either one of the following A) and B) is met. Both of A) and B) may be met.

A) The electrode 23 is provided on an inner side surface of each of the micro-chambers 26.

B) The electrode 23 is provided as a transparent electrode on a bottom surface of each of the micro-chambers 26.

In the case of employing the above A, that is, such a configuration that the electrode is provided on an inner side surface of the micro-chamber, attenuation of light passing through the bottom surface becomes less than in the case of employing a transparent electrode as in the above B; so, in the former case, the measurement sensitivity is improved. In the above B, in the case where the hydrophilicity of the transparent electrode surface is low, a problem of escape of the liquid from the micro-chamber may possibly arise; but, in the case where the electrode is provided on the inner side surface of the micro-chamber as in the above A, such a problem can be lessened.

In an example illustrated in FIG. 2, the electrode 23 is provided on the inner side surface of each of the micro-chambers 26. The electrode 23 may be constituted of a metal. As the metal, for example, copper, silver, gold, platinum, aluminum, chromium or silver chloride can be used. The electrode 23 may be constituted of a material other than a metal, specifically, for example, ITO (indium tin oxide), IZO (a material composed of indium tin oxide and zinc oxide), ZnO or IGZO (a material constituted of indium, gallium, zinc and oxygen).

The thickness of the electrode 23 may be, for example, 10 nm or larger and 100 μm or smaller, or 100 nm or larger and 5 μm or smaller, or 250 nm or larger and 1 μm or smaller.

In such a configuration, light entering the substrate 22 from below the substrate 22 is transmitted through the substrate 22 and penetrates into the interiors of the micro-chambers 26, and light entering the substrate 22 from the interiors of the micro-chambers 26 is transmitted through the substrate 22 and escapes toward below the substrate 22.

By applying a voltage by using the electrode 23, a reaction in the micro-chambers 26 is enabled to be promoted. Hence, the high-density micro-chamber array 20 can also be applied to a detection apparatus, a cultivation apparatus and the like.

Figure 3:
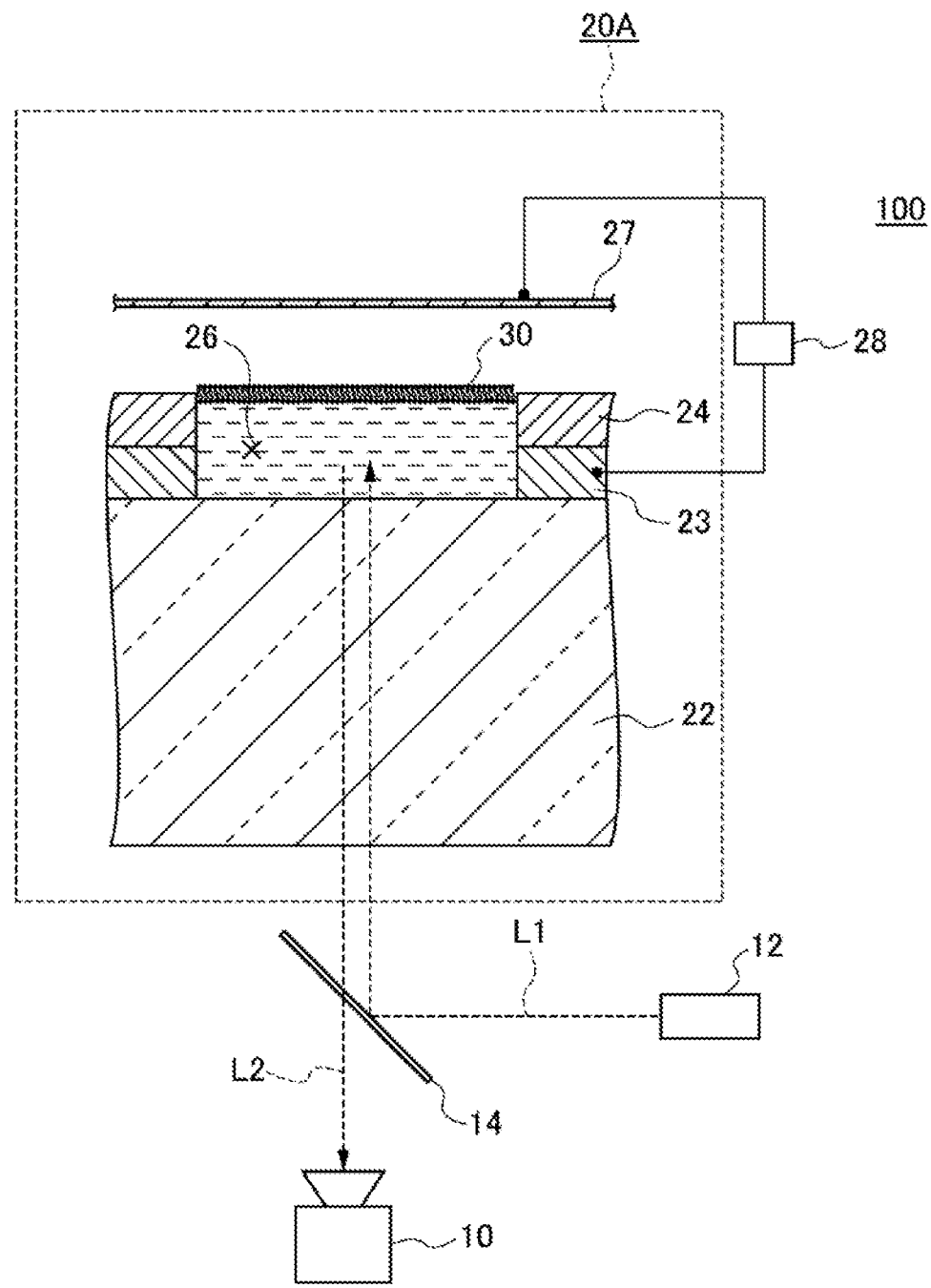
FIG. 3 is a conceptual view illustrating one example of the high-density micro-chamber array system according to the first embodiment.

FIG. 3 is a conceptual view illustrating one example of a high-density micro-chamber array system according to the first embodiment. In the modified example illustrated in FIG. 3, a high-density micro-chamber array 20A has, in addition to the configuration of a high-density micro-chamber array 20, a counter electrode 27 above a lipid bilayer membrane 30. Hereinafter, by reference to FIG. 3, the high-density micro-chamber array system 100 according to the first embodiment will be described.

As illustrated as an example in FIG. 3, the high-density micro-chamber array system 100 has a substrate 22, a hydrophobic layer 24, a lipid bilayer membrane 30, an electrode 23, a counter electrode 27 and a voltage-applying apparatus 28. The substrate 22, the hydrophobic layer 24, the lipid bilayer membrane 30 and the electrodes 23 are as described above, so detailed descriptions thereof are omitted.

The counter electrode 27 is an electrode provided above the lipid bilayer membrane 30. The counter electrode 27 may be provided in such a way as to extend over a plurality of micro-chambers 26. The counter electrode 27 may be provided in such a way as to extend over all micro-chambers 26. The size and shape of the counter electrode 27 as viewed in the thickness direction may coincide nearly with those of the substrate 22. The counter electrode 27 may be constituted of a metal. As the metal, for example, copper, silver, gold, aluminum or chromium can be used. The distance from the substrate 22 to the counter electrode 27 may be, for example, 1 μm or longer and 10 mm or shorter, or 2 μm or longer and 1 mm or shorter, or 10 μm or longer and 100 μm or shorter.

The counter electrode 27 may be provided in such a way as to correspond to each of the micro-chambers 26. Specifically, for example, in the case where a pair of micro-chamber devices (see FIG. 1 and FIG. 2) according to the present embodiment are laminated so that openings of the one micro-chamber face openings of the other micro-chamber device, the electrode of the one micro-chamber device may be used as the electrode 23 and the electrode of the other micro-chamber device may be used as the counter electrode 27.

The voltage-applying apparatus 28 applies a voltage between the electrode 23 and the counter electrode 27. The voltage-applying apparatus 28 may be, for example, one to apply a direct-current voltage. As the voltage-applying apparatus 28, specifically, for example, a function generator (for example, manufactured by NF Corp.) can be used.

By applying a voltage between the electrode 23 and the counter electrode 27, a reaction in the micro-chambers 26 is enabled to be promoted. Hence, the high-density micro-chamber array system 100 can also be applied to a detection apparatus, a cultivation apparatus and the like.

Modified Example

Figure 4:
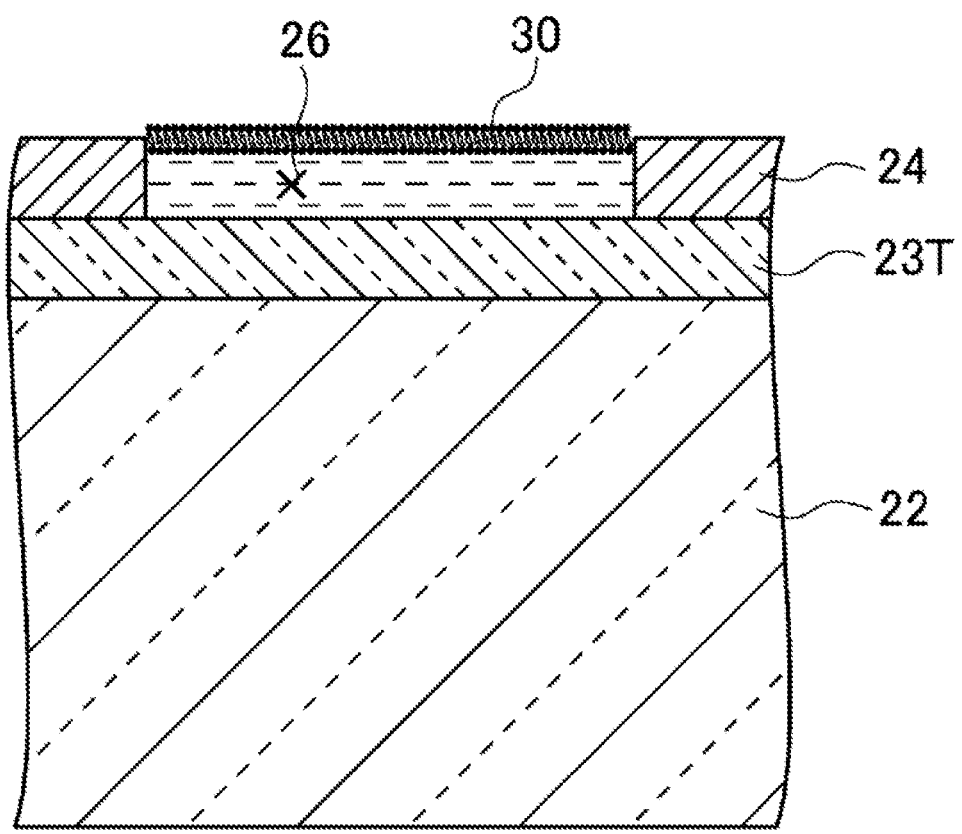
FIG. 4 is a plan view illustrating a schematic configuration of a high-density micro-chamber array according to a modified example of the first embodiment.

FIG. 4 is a plan view illustrating a schematic configuration of a high-density micro-chamber array according to a modified example of the first embodiment. Hereinafter, by reference to FIG. 4, a high-density micro-chamber array 20B according to the modified example will be described.

In an example illustrated in FIG. 4, the high-density micro-chamber array 20B has a substrate 22, a hydrophobic layer 24, a lipid bilayer membrane 30 and an electrode 23T. The substrate 22, the hydrophobic layer 24 and the lipid bilayer membrane 30 are as described above, so detailed descriptions thereof are omitted.

The electrode 23T is provided as a transparent electrode on the bottom surface of each of the micro-chambers 26. In the example illustrated in FIG. 4, the electrode 23T is configured to cover the entire surface of the substrate 22. The electrode 23T can be constituted of ITO (indium tin oxide), IZO (a material composed of indium tin oxide and zinc oxide), ZnO, IGZO (a material constituted of indium, gallium, zinc and oxygen), or the like.

Also in such a configuration, light entering the substrate 22 from below the substrate 22 is transmitted through the substrate 22 and the electrode 23T and penetrates into the interior of the micro-chamber 26, and light entering the electrode 23T and substrate 22 from the interior of the micro-chamber 26 is transmitted through the electrode 23T and the substrate 22 and escapes toward below the substrate 22.

In the present modified example, the thickness of the electrode 23T is not especially limited as long as light entering the substrate 22 from below the substrate 22 is capable of being transmitted through the substrate 22 and penetrating into the interior of the micro-chamber 26, and light entering the substrate 22 from the interior of the micro-chamber 26 is capable of being transmitted through the substrate 22 and escaping toward below the substrate 22.

Here, the electrode provided on the inner side surface of the micro-chamber 26 and the electrode provided as a transparent electrode on the bottom surface thereof may be combined and configured as one electrode. Specifically, for example, the electrode 23 illustrated in FIG. 2 and the electrode 23T illustrated in FIG. 4 may be combined and configured as one electrode.

[Manufacturing Method]

Figure 5:
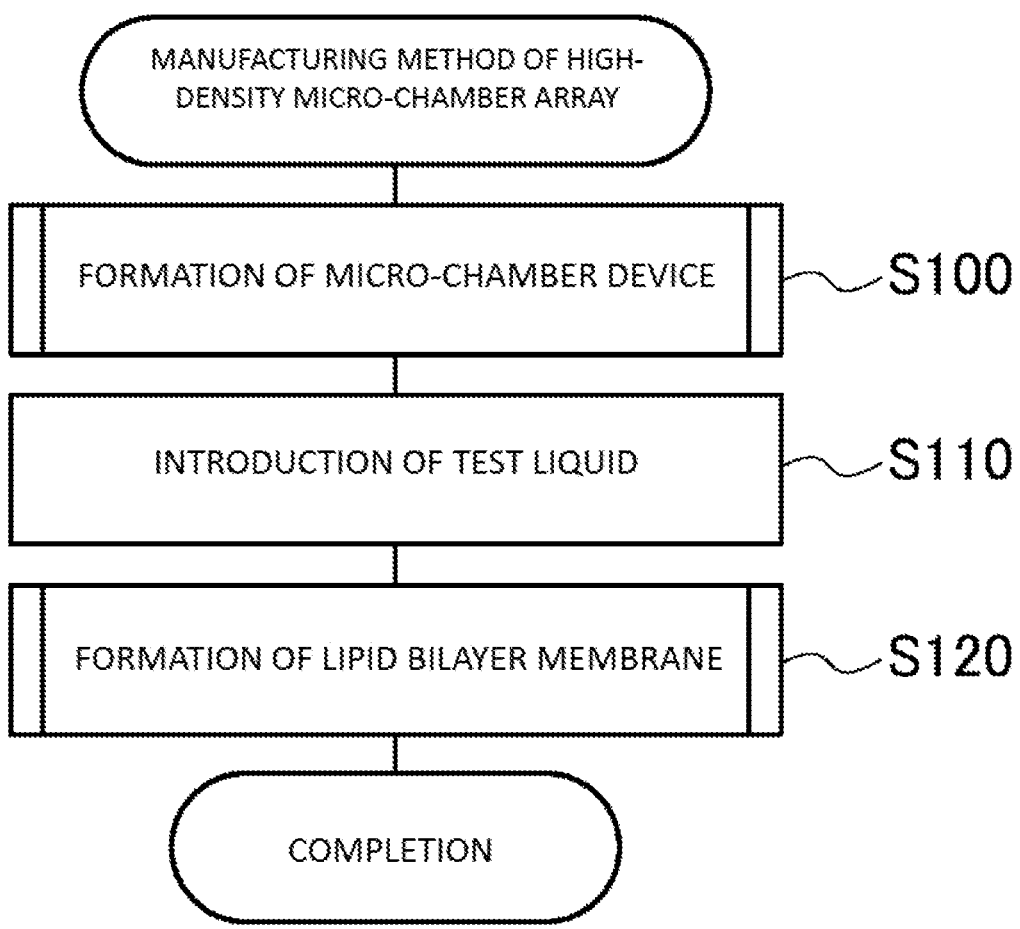
FIG. 5 is a process diagram showing one example of a manufacturing method of a high-density micro-chamber array according to the first embodiment.

Hereinafter, a manufacturing method of the high-density micro-chamber array 20 of the first embodiment will be described. FIG. 5 is a process diagram showing one example of a manufacturing method of the high-density micro-chamber array according to the first embodiment.

The high-density micro-chamber array 20 of the first embodiment is completed by first forming a micro-chamber device in which each opening is not liquid-sealed with a lipid bilayer membrane 30 (step S100), introducing a test liquid to the formed micro-chamber device (step S110), and forming the lipid bilayer membrane 30 in such a way as to liquid-seal the opening of each micro-chamber 26 in the state of being filled with the test liquid (step S120). The formation of the micro-chamber device (step S100) is carried out, for example, by a process diagram shown in FIG. 6; and the formation of the lipid bilayer membrane 30 (step S120) is carried out, for example, by a process diagram shown in FIG. 7. Hereinafter, the formation of the micro-chamber device will be described and thereafter, the formation of the lipid bilayer membrane 30 will be described.

1. Formation of a Micro-Chamber Device

The step of forming a micro-chamber device can involve, for example, forming thin films of an electrode material and a hydrophobic substance in order on the surface of a substrate 22, forming a resist on a portion of the thin film surface excluding portions thereof where a plurality of micro-chambers 26 are to be formed, forming one sections of the plurality of micro-chambers 26 in the thin film of the hydrophobic substance by dry etching, removing the resist, and further forming remainder sections of the plurality of micro-chambers 26 in the thin film of the electrode material by wet etching using the layer of the hydrophobic substance as a mask. In such a process, the high-density micro-chamber array 20 can be manufactured highly precisely and relatively easily. Here, it is natural that part of the plurality of micro-chambers 26 may be formed in the thin film of the hydrophobic substance by using means other than dry etching, for example, means such as nanoimprinting.

Figure 6:
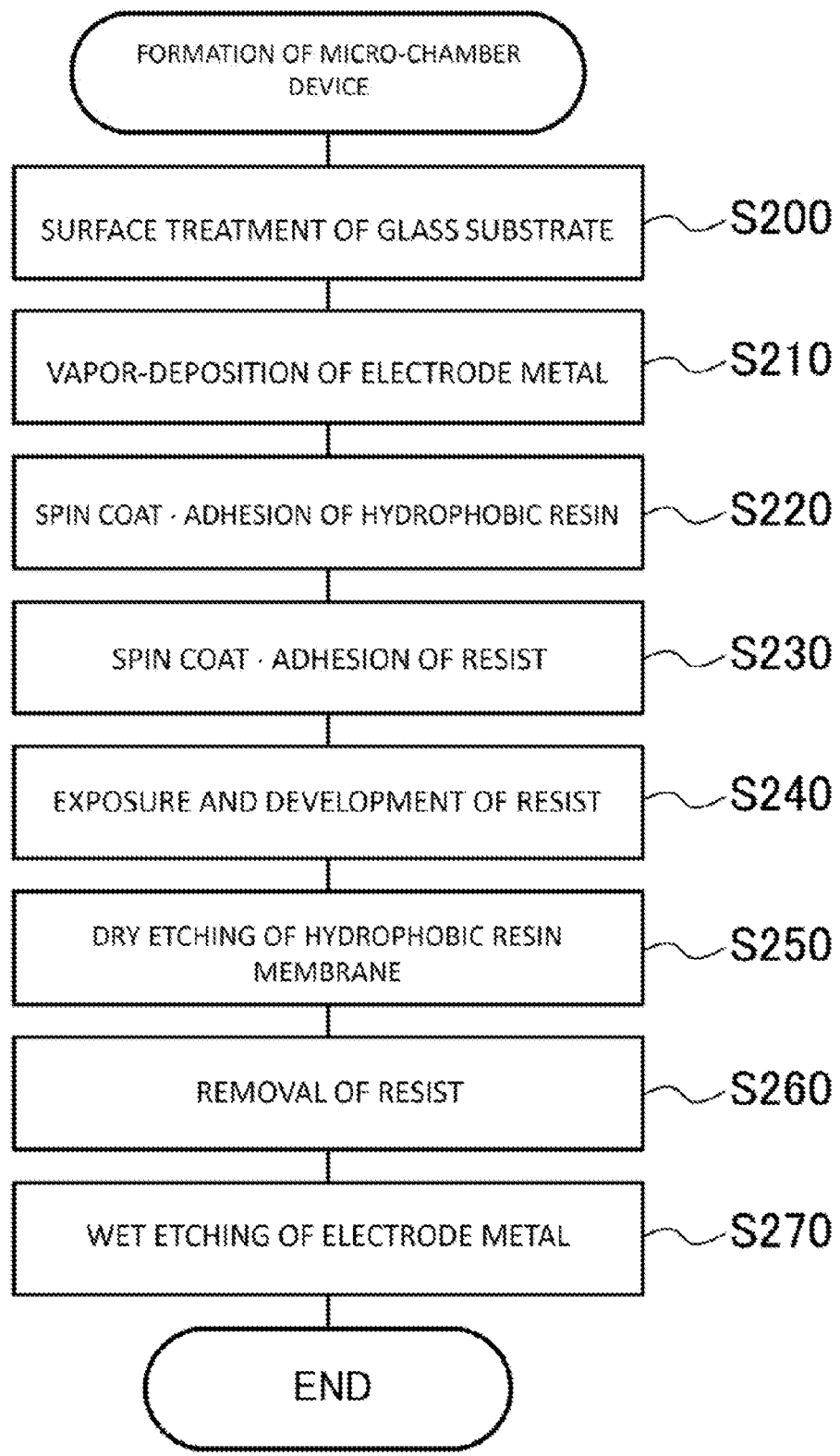
FIG. 6 is a process diagram showing one example of formation (step S100) of a micro-chamber device in the first embodiment.

FIG. 6 is a process diagram (steps S200 to S270) showing one example of the formation of the micro-chamber device (step S100) in the first embodiment. FIG. 8A to FIG. 8H illustrate the state of each of the steps of forming the micro-chamber device. The formation of the micro-chamber device involves first soaking a glass substrate 22 for about 24 hours in a 10M potassium hydroxide (KOH) solution as a surface treatment to clean the glass surface of the glass substrate 22 (step S200, FIG. 8A)

Figure 8A:
FIG. 8A is a view illustrating a step of providing a substrate in formation of a micro-chamber device of the first embodiment.
Figure 8B:
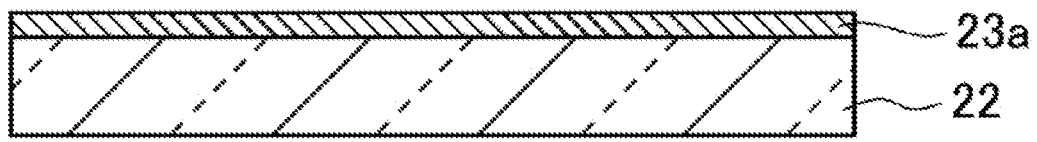
FIG. 8B is a view illustrating a step of forming an electrode layer on the substrate in the formation of the micro-chamber device of the first embodiment.

Then, an electrode layer 23a is formed by vapor-depositing a metal on the surface of the glass substrate 22 by using a vacuum deposition apparatus (step S210, FIG. 8B). As the kind of the metal, for example, silver, gold, chromium or the like can be used. The thickness can be made to be, for example, about 500 nm.

Figure 8C:
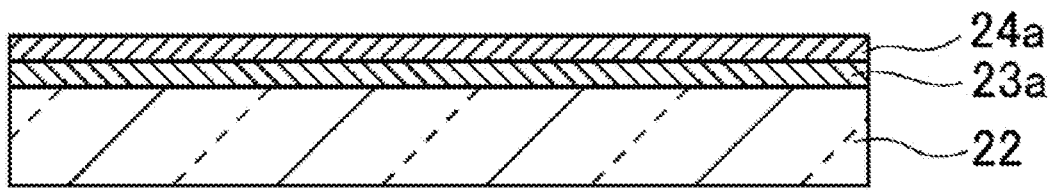
FIG. 8C is a view illustrating a step of forming a substance membrane on the electrode layer in the formation of the micro-chamber device of the first embodiment.

Then, a substance membrane 24a is formed by spin-coating a hydrophobic substance (for example, a fluororesin (CYTOP), manufactured by Asahi Glass Co., Ltd.), and is adhered on the surface of the electrode layer 23a (step S220, FIG. 8C). As the condition of the spin-coating, one can use, for example, 4,000 rps (revolution per second) for 30 sec. In this case, the membrane thickness of the substance membrane 24a becomes about 500 nm. The adhesion of the substance membrane 24a on the surface of the electrode layer 23a can be carried out, for example, by 1 hour of baking on a hot plate at 180° C.

Figure 8D:
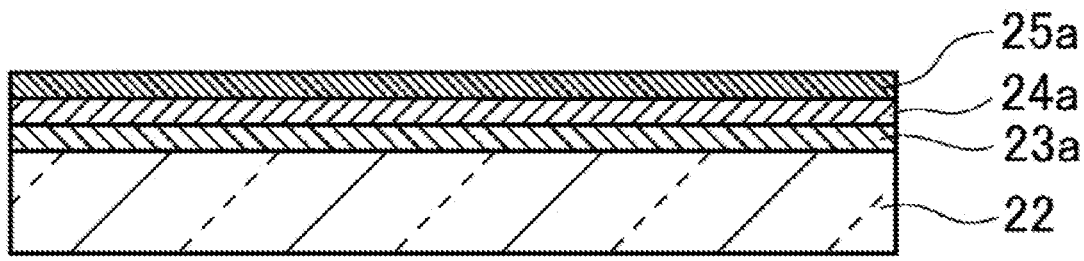
FIG. 8D is a view illustrating a step of forming a resist on the substance membrane in the formation of the micro-chamber device of the first embodiment.

Then, a resist 25a is formed on the surface of the substance membrane 24a by spin-coating, and is adhered on the surface of the substance membrane 24a (step S230, FIG. 8D). As the resist 25a, AZ-4903, manufactured by AZ Electronic Materials SA, or the like can be used. As the condition of the spin-coating, one can use, for example, 4,000 rps (revolution per second) for 60 sec. The adhesion of the resist 25a on the surface of the substance membrane 24a can be carried out, for example, by 5 min of baking on a hot plate at 110° C. to evaporate an organic solvent in the resist 25a.

Figure 8E:
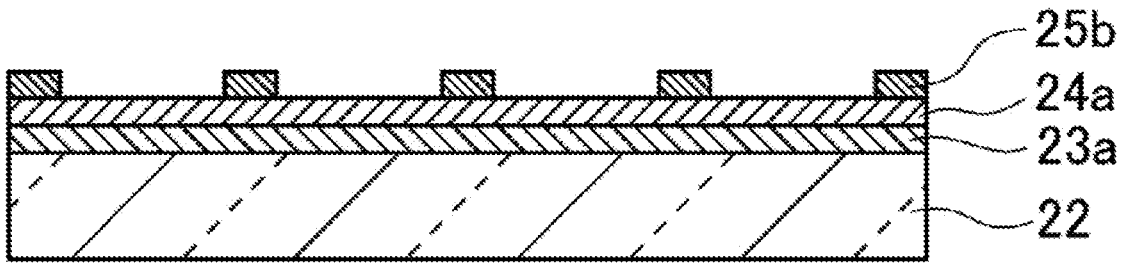
FIG. 8E is a view illustrating a step of patterning the resist in the formation of the micro-chamber device of the first embodiment.
Figure 8F:
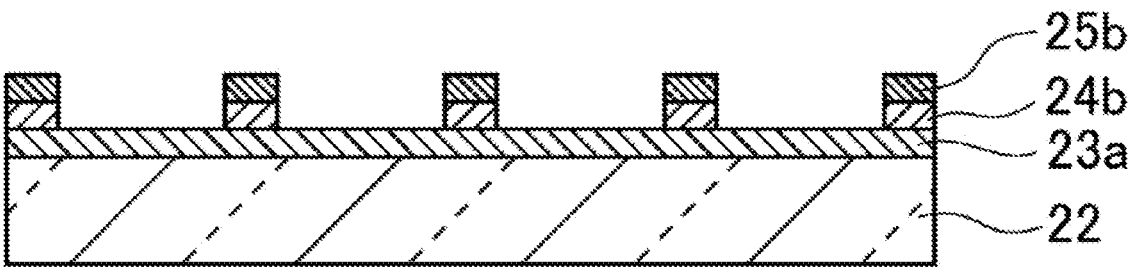
FIG. 8F is a view illustrating a step of etching the substance membrane with the patterned resist being used as a mask in the formation of the micro-chamber device of the first embodiment.

Then, the resist 25a is exposed by using a mask having a pattern of the micro-chambers 26, and soaked in a developer exclusive for resist to thereby form a resist 25b in which portions where the micro-chambers 26 are to be formed have been removed (step S240, FIG. 8E). As the condition of the exposure, one can use, for example, irradiation of a UV power of 250 W for 7 sec by using an exposure machine, manufactured by San Ei Giken Inc. As the condition of the development, one can use, for example, soaking in an AZ developer, manufactured by AZ Electronic Materials SA, for 5 min.

Figure 8G:
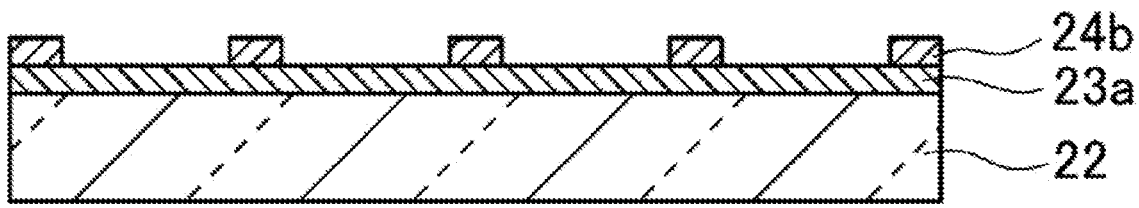
FIG. 8G is a view illustrating a step of removing the resist in the formation of the micro-chamber device of the first embodiment.

Then, the substance membrane 24a masked with the resist 25b is dry-etched to make a substance membrane 24b in which the portions to become the micro-chambers 26 have been removed (step S250, FIG. 8F); and the resist 25b is removed (step S260, FIG. 8G). The dry-etching can be carried out under the etching condition of $O_2$: 50 sccm, pressure: 10 Pa, power: 50 W and time: 30 min by using a reactive ion etching apparatus, manufactured by Samco Inc. The removal of the resist 25b can be carried out by soaking in acetone, and washing with isopropanol and thereafter washing with pure water.

Figure 8H:
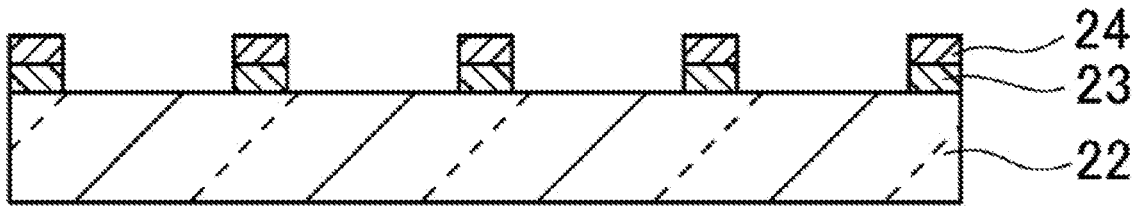
FIG. 8H is a view illustrating a step of etching the electrode layer with the patterned substance membrane being used as a mask in the formation of the micro-chamber device of the first embodiment.

Then, the metal layer 23a is wet-etched to thereby complete the micro-chambers 26 (step S270, FIG. 8H). The wet-etching can be carried out, for example, by soaking the micro-chamber device in the course of being formed, in a metal etchant, and thereafter washing with pure water.

Such a method can complete the micro-chamber device in which the plurality of micro-chambers 26 are formed on the surface of glass substrate 22 by the hydrophobic layer 24 and the electrode 23.

The shape and size of the micro-chambers 26 may suitably be determined according to the magnitude of the reaction rate of a biomolecule, and the like. The micro-chambers 26 may be formed in such a way as to have, for example, a depth D of 10 μm and a diameter R of 40 μm, or a depth D of 2 μm and a diameter R of 10 μm. The smallest size of practical and feasible micro-chambers 26 is conceivably both a depth D and a diameter R of about several hundred nanometers. In consideration of the magnitude of the reaction rate of a biomolecule as a test object and the content of the biomolecule and also in consideration of easiness of their manufacture, it is conceivable that the depth and the diameter of the micro-chambers 26 are practically suitably several hundred nanometers to several micrometers. Therefore, the micro-chambers 26 suffice if being formed so that the depth is in a predetermined depth region including 500 nm and the equivalent-circle diameter is in a predetermined diameter range including 1 μm.

The "predetermined depth range" suffices if being thought to be in the order including 500 nm; and there may be used, for example, a range of 50 nm, being 0.1 time 500 nm, or larger and 5 μm, being 10 times 500 nm, or smaller, or a range of 250 nm, being 0.5 time 500 nm, or larger and 1 μm, being 2 times 500 nm, or smaller.

The "predetermined thickness range" is not especially limited, and may be, for example, 10 nm or larger and 500 nm or smaller, or 20 nm or larger and 500 nm or smaller, or 30 nm or larger and 500 nm or smaller. The "predetermined thickness range" may be, for example, 10 nm or larger and 100 nm or smaller, or 20 nm or larger and 100 nm or smaller, or 30 nm or larger and 100 nm or smaller. When the depth of the micro-chamber is made to be small (several tens of nanometer) and the capacity thereof is made to be small (about several hundred attoliters), the measurement sensitivity is further improved (Soga, N., et al., 2015, Attolitre-sized lipid bilayer chamber array for rapid detection of single transporters, Scientific Reports, 5:11025).

The "predetermined diameter range" suffices if being thought to be in the order including 1 μm; and there may be used, for example, a range of 100 nm, being 0.1 time 1 μm, or larger and 10 μm, being 10 times 1 μm, or smaller, or a range of 500 nm, being 0.5 time 1 μm, or larger and 2 μm, being 2 times 1 μm, or smaller.

Since the detection sensitivity to a reaction of a biomolecule is inversely proportional to the number of the molecule in the micro-chamber 26, it is conceivably preferable that the largest capacity L of the micro-chamber 26 practical and feasible in order to detect the biomolecular reaction at a high sensitivity is about $4,000 \times 10^{-18}$ [$m^3$]. For example, an experiment was carried out by forming micro-chambers (capacity L: $3,532.5 \times 10^{-18}$ [$m^3$]) having a depth of 5 μm and a diameter R of 30 μm, and a good detection sensitivity to a biomolecular reaction could be attained. In this case, when the interval between adjacent micro-chambers is taken to be 4 μm, the area S necessary for one micro-chamber becomes a square of 34 μm in one side, and is calculated as $S=(34 \times 10^{-6})^2$ [$m^2$]$=1,156 \times 10^{-12}$ [m]. Therefore, on the glass substrate, about $0.86 \times 10^5$ per $cm^2$ ($1 \times 10^{-4}$ [$m^2$]) of the micro-chambers is resultantly formed; and even if the frequency of occurrence of the biomolecular reaction is low, since the reaction occurs in some of the chambers, the micro-chambers become capable of detecting the biomolecular reaction at a high sensitivity.

2. Formation of a Lipid Bilayer Membrane 30

A formation step of a lipid bilayer membrane 30 involves, for example, making a test liquid to flow through a liquid channel 48 forming its nearly horizontal bottom surface provided by a surface on which the plurality of micro-chambers 26 are formed to fill the plurality of micro-chambers 26 with the test liquid, making a lipid-containing organic solvent containing a lipid to form a lipid bilayer membrane 30 to flow through the liquid channel 48 to thereby form a first lipid membrane 32, in such a state that hydrophilic groups of the lipid are directed toward the test liquid side of the plurality of micro-chambers 26, in each opening of the plurality of micro-chambers 26, and making a membrane-forming liquid to flow through the liquid channel 48 to thereby form a second lipid membrane 34, in such a state that hydrophobic groups of the lipid are directed toward the first lipid membrane 32 side, in such a way as to be stacked on the first lipid membrane 32, to thereby form the lipid bilayer membrane 30.

Figure 7:
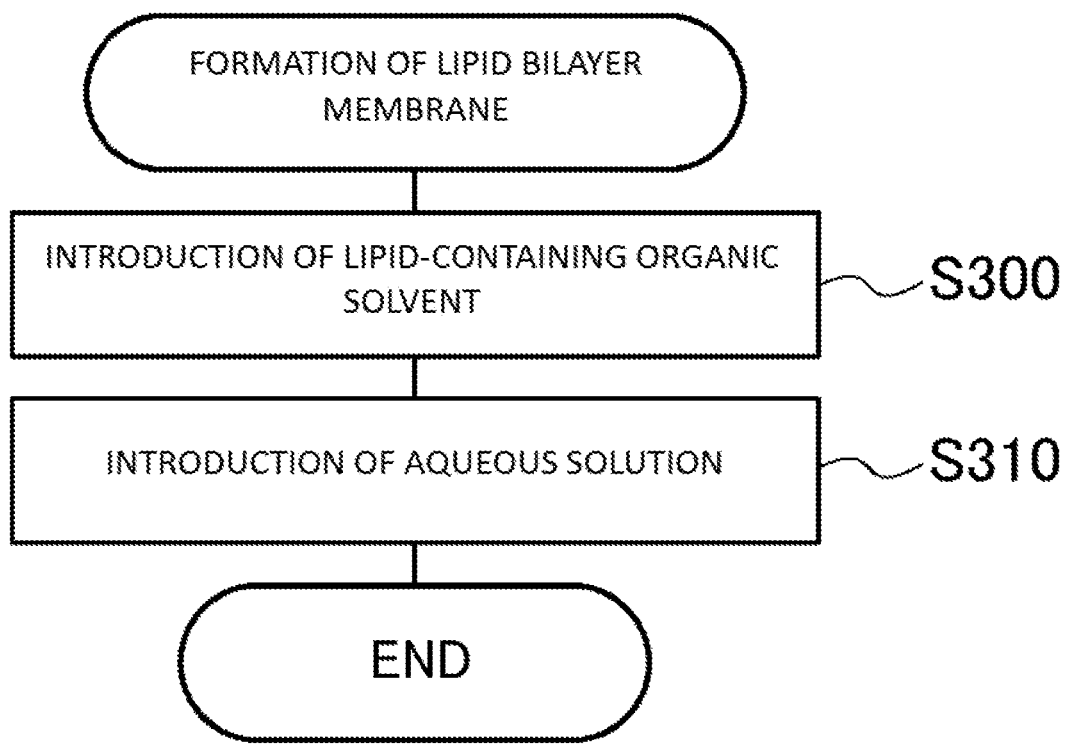
FIG. 7 is a process diagram showing one example of formation (step S120) of a lipid bilayer membrane in the first embodiment.
Figure 9A:
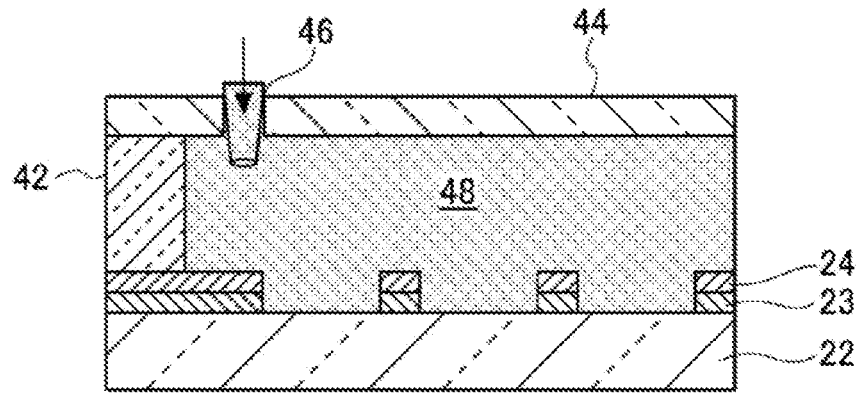
FIG. 9A is a view illustrating a step of filling a liquid channel with a test liquid in formation of a lipid bilayer membrane in a high-density micro-chamber array according to the first embodiment.
Figure 9B:
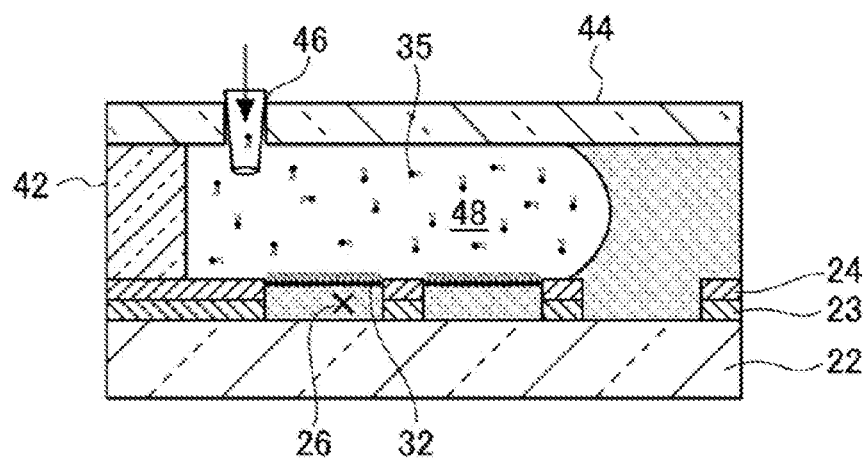
FIG. 9B is a view illustrating a step of introducing an organic solvent containing a lipid in the formation of the lipid bilayer membrane in the high-density micro-chamber array according to the first embodiment.
Figure 9C:
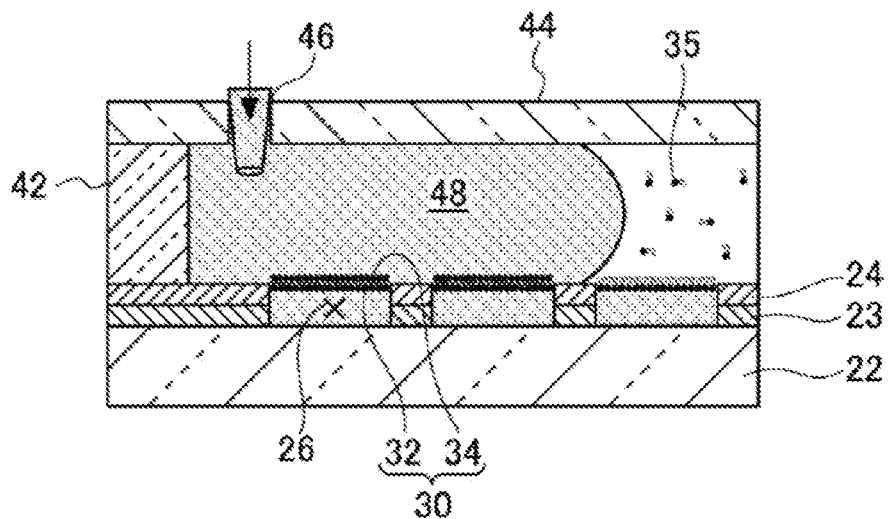
FIG. 9C is a view illustrating a step of introducing a membrane-forming liquid in the formation of the lipid bilayer membrane in the high-density micro-chamber array according to the first embodiment.

FIG. 7 is a process diagram (steps S300 to S310) showing one example of the formation (step S120) of the lipid bilayer membrane 30 in the first embodiment. FIGS. 9A to 9C illustrate the state of each step of forming the lipid bilayer membrane 30. As a pre-stage of forming the lipid bilayer membrane 30, a glass plate 44 having a liquid-introducing hole 46 formed therein is mounted on the micro-chamber device through a spacer 42. Thereby, there is formed the liquid channel 48 whose nearly horizontal bottom surface is formed by a surface on which the micro-chambers 26 of the micro-chamber device are formed. The test liquid is introduced from the liquid-introducing hole 46 to fill the liquid channel 48 with the test liquid (FIG. 9A). Here, the composition of the test liquid can be, for example, an aqueous solution; specifically, there can be used various types of liquids, for example, a liquid containing a 10 mM pH buffer (pH: 5 to 9), a 20 μM fluorescent indicator (Ca1520, pHrodo or the like) and a 10 mM sodium chloride.

An organic solvent containing a lipid 35 is introduced from the liquid-introducing hole 46 in such a state that the liquid channel 48 is filled with the test liquid (step S300 of FIG. 7, FIG. 9B). Here, as the lipid 35, there can be used natural lipids derived from soybeans, *Bacillus coli* and the like, and artificial lipids such as DOPE (dioleoylphosphatidylethanolamine) and DOPG (dioleoylphosphatidylglycerol). As the organic solvent, hexadecane and chloroform can be used. When the organic solvent containing the lipid 35 is introduced, the opening of the micro-chamber 26 is liquid-sealed with a first lipid membrane 32 in such a state that hydrophilic groups of the lipid 35 are directed toward the micro-chamber 26 side in a state where the micro-chamber 26 is filled with the test liquid.

Then, a membrane-forming liquid to form a lipid bilayer membrane 30 is introduced from the liquid-introducing hole 46 (step S310 of FIG. 7, FIG. 9C) to thereby form the lipid bilayer membrane 30. As the composition of the membrane-forming liquid, for example, a liquid containing a 10 mM pH buffer (pH: 5 to 9) and a 10 mM sodium chloride can be used. Here, the high-density micro-chamber array 20 according to the first embodiment is completed by removing the glass plate 44 and the spacer 42 after the lipid bilayer membranes 30 are formed.

After the formation step of the lipid bilayer membrane 30, a reconstitution step of reconstituting a membrane protein in the lipid bilayer membrane 30 can also be included. In such a configuration, there can be obtained the high-density micro-chamber array 20 in which the lipid bilayer membranes 30 have the membrane protein reconstituted therein. Such a high-density micro-chamber array 20 in which the lipid bilayer membranes 30 have the membrane protein reconstituted therein can be used for detection of biomolecular reactions and the like through the membrane protein. In the case of using such a form, the reconstitution step may be a step of introducing any of a cell membrane fragment containing a membrane protein, a lipid bilayer membrane embedded with a protein, a water-soluble protein, a liposome incorporated with a protein or a protein solubilized with a surfactant into the lipid bilayer membrane 30 to thereby incorporate the protein, as a membrane protein, in the lipid bilayer membrane 30. As means to incorporate the protein in the lipid bilayer membrane, in the case of a liposome, membrane fusion or the like can be used, and in the case of the protein solubilized with a surfactant, thermal fluctuation or the like can be used.

According to the manufacturing method of the high-density micro-chamber array 20 of the first embodiment, having been described hitherto, there can relatively easily be manufactured the high-density micro-chamber array 20 in which a large number of micro-chambers 26 liquid-sealed with the lipid bilayer membrane 30 and having a very small capacity are formed at a high density.

According to the high-density micro-chamber array 20 of the first embodiment, since the capacity L of each of the micro-chambers 26 is as small as $19.6 \times 10^{-18}$ [m$^3$], by using the high-density micro-chamber array 20 of the first embodiment for detection of a biomolecular reaction, the number of biomolecules in the micro-chambers 26 can be made to be small. Consequently, the degree of the concentration change in the micro-chamber 26 by the reaction of one biomolecule can be raised, and the detection sensitivity when the reaction is detected as the concentration change can be increased. Even if the reaction of the biomolecule is remarkably slow, the reaction of the biomolecule can be detected at a high sensitivity. Further since the configuration is made in such a way as to have the array in which such minute micro-chambers 26 are formed at as high a density as about $2 \times 10^6$ per cm$^2$ ($1 \times 10^{-4}$ [m$^2$]) in large numbers, even if the frequency of occurrence of the biomolecular reaction is low, the reaction occurs in some of the micro-chambers 26; therefore, the biomolecular reaction can be detected at a high sensitivity.

[Analysis Method of a Membrane Protein]

The high-density micro-chamber array 20 of the first embodiment, further by reconstituting a membrane protein in the lipid bilayer membrane 30, can be used for analysis of the membrane protein. That is, an analysis method of the membrane protein according to the first embodiment involves providing the high-density micro-chamber array of the first embodiment, and forming the lipid bilayer membranes on the openings of the plurality of micro-chambers. The lipid bilayer membranes are made to hold the membrane protein. Thereupon, by applying a voltage between the electrode and the counter electrode provided above the lipid bilayer membranes, the properties of the membrane protein are changed.

The properties of the membrane protein can include, for example, the transport characteristic of substances through the lipid bilayer membrane, the catalytic characteristic of the membrane protein, and the conformation of the membrane protein.

First, means to reconstitute a membrane protein in the lipid bilayer membrane 30 will be described. As means to incorporate a protein in the lipid bilayer membrane, in the case of a liposome, membrane fusion or the like can be used, and in the case of a protein solubilized with a surfactant, thermal fluctuation or the like can be used. Hereinafter, the means will be described more specifically.

The reconstitution of a membrane protein can be carried out by introducing 50 μL in capacity of a solution of the membrane protein reconstituted in a liposome from the liquid-introducing hole 46 of the glass plate 44 in such a state that the liquid channel 48 is formed by mounting the glass plate 44 on the micro-chamber device through the spacer 42 (see FIG. 9A), and incubating the system for 1 hour to thereby incorporate the membrane protein in the lipid bilayer membrane 30 by membrane fusion.

As illustrated in FIG. 9A, the liquid channel 48 is formed between the hydrophobic layer 24 and a ceiling provided above the hydrophobic layer 24. The liquid channel 48 may be a space having a certain thickness. In the example illustrated in FIG. 9A, the ceiling is the lower surface of the glass plate 44.

In order to efficiently form a uniform lipid membrane, an aqueous solution and a lipid solution need to be made to flow at a constant flow rate. By disposing the liquid channel above the micro-chambers, the liquid can be supplied simultaneously and uniformly to all the micro-chambers. Thereby, the lipid membrane is enabled to be efficiently formed.

In the case of forming a functional lipid membrane, the lipid membrane needs to be made thin. For the thickness reduction, a shearing force by the liquid is effective. By disposing the liquid channel, the aqueous solution can be made to flow on the lipid membrane, and the lipid membrane is enabled to be efficiently made thin by the shearing force.

By patterning a metal on the ceiling of the channel, the counter electrode 27 can easily be provided. For example, a counter electrode may be formed on the surface of the glass substrate 44. The counter electrode 27 can be utilized for the control of the membrane potential and the operations of other biomolecules.

As a composition of a solution of a membrane protein, there can be used, for example, a solution containing a 10 nM FoF1 (an ATP synthase being the membrane protein), a 1 mM MOPS (3-morpholinopropane-1-sulfonic acid) of a pH of 7, a 10 mM sodium chloride (NaCl) and a 2 mM magnesium chloride (MgCl$_2$).

When the configuration is made such that the membrane protein is thus reconstituted in the lipid bilayer membranes 30 of the high-density micro-chamber array 20 of the first embodiment, the high-density micro-chamber array 20 of the first embodiment can be used for detection of a biomolecular reaction or the like through the membrane protein.

Here, the means to reconstitute a membrane protein in the lipid bilayer membrane 30 is not limited to a method of using a liposome. The membrane protein may be reconstituted in the lipid bilayer membrane 30, for example, by introducing a membrane protein solubilized with a surfactant, a water-soluble protein or the like. For example, in the case where the membrane protein solubilized with a surfactant is reconstituted in the lipid bilayer membrane 30, it suffices if 50 µL in capacity of the membrane protein solution solubilized with a surfactant is introduced from the liquid-introducing hole 46 of the glass plate 44 and the system is incubated for 1 hour to thereby incorporate the membrane protein in the lipid bilayer membrane 30 by thermal fluctuation. As a composition of the solution of the membrane protein, there can be used, for example, a solution containing a 10 nM FoF1 (an ATP synthase being the membrane protein), a 0.01 to 0.1% n-decyl-β-maltoside (a surfactant), a 1 mM MOPS (3-morpholinopropane-1-sulfonic acid) of a pH of 7, a 10 mM sodium chloride (NaCl) and a 2 mM magnesium chloride ($MgCl_2$).

Means to reconstitute a membrane protein in the lipid bilayer membrane 30 of the high-density micro-chamber array 20 of the first embodiment may involve using a protein-containing liquid as a test liquid in the state that at least a protein is solubilized or suspended in the test liquid, in a stage before the lipid bilayer membranes 30 are formed on the micro-chamber device, that is, in a stage where the test liquid is introduced from the liquid-introducing hole 46 to fill the liquid channel 48 with the test liquid. That is, by introducing the protein-containing liquid as a test liquid from the liquid-introducing hole 46, the liquid channel 48 is put in the state of being filled with the protein-containing liquid. By introducing an organic solvent containing a lipid 35 and a membrane-forming liquid (which may be a membrane-forming aqueous solution) for forming the lipid bilayer membranes 30 in order from the liquid-introducing hole 46, the openings of the micro-chambers 26 are liquid-sealed with the lipid bilayer membranes 30 in such a state that the protein-containing liquid is filled in the micro-chambers 26. The micro-chambers 26 are liquid-sealed with the lipid bilayer membranes 30, and the protein in the protein-containing liquid in the micro-chambers 26 is reconstituted in the lipid bilayer membranes 30 by membrane fusion, thermal fluctuation or the like. Here, as the protein in the protein-containing liquid, there can be used, for example, a cell membrane fragment containing a membrane protein, a lipid bilayer membrane embedded with a protein, a water-soluble protein, a liposome incorporated with a protein or a protein solubilized with a surfactant.

According to the high-density micro-chamber array of the first embodiment, by applying a voltage between the electrode 23 and the counter electrode 27 provided above the lipid bilayer membranes 30, the properties of the membrane protein can be changed. The application voltage can suitably be regulated, for example, between −300 mV and +300 mV.

Here, light entering the substrate 22 from below the substrate 22 is transmitted through the substrate 22 and the electrode 23T and penetrates into the interiors of the micro-chambers 26, and light entering the electrode 23T and the substrate 22 from the interiors of the micro-chambers 26 is transmitted through the electrode 23T and the substrate 22 and escapes toward below the substrate 22. The change in the properties of the membrane protein can be analyzed by using a confocal laser microscope and detecting light emitted from a fluorescent substance contained in the test liquid accommodated in the interiors of the micro-chambers 26, and so on. As the microscope, an epi-illumination type confocal microscope may be used.

Specifically, as illustrated in FIG. 3, light L1 emitted from a laser light source 12 is reflected from a dichroic mirror 14 and enters the substrate 22. The light having entered the substrate 22 is transmitted through the substrate 22 and penetrates into the micro-chamber 26. A fluorescent substance in the micro-chamber 26 receives the penetrating light, and radiates light having a different wavelength. The radiated light L2 enters the substrate 22, is transmitted through the substrate 22, and escapes toward below the substrate 22. Further, the light is transmitted through the dichroic mirror 14 and reaches a camera 10. Here, between the laser light 12 source and the dichroic mirror 14, and between the dichroic mirror 14 and the camera 10, optical systems may suitably be inserted.

1. First Experimental Example

In a first Experimental Example, by using the high-density micro-chamber array 20A (see FIGS. 1, 2 and 3) of the first embodiment, and a fluorescent membrane potential indicator, the detection of the membrane potential was carried out. The experimental condition of the present Experimental Example was as follows.

Material of a substrate 22: colorless glass
Thickness of the substrate 22: 0.12 mm
Shape of the substrate 22: a rectangle of 24 mm×32 mm
Material of a counter electrode 27: gold
Shape of the counter electrode: a rectangle of 18 mm×18 mm
Distance from the substrate 22 to the counter electrode 27: 0.2 mm
Material of a hydrophobic layer 24: a fluororesin (CYTOP), manufactured by Asahi Glass Co., Ltd.
Thickness of the hydrophobic layer: about 500 nm
Material of an electrode 23: gold
Thickness of the electrode 23: about 500 nm
Micro-chamber: a cylindrical shape of about 5 µm in diameter and about 1 µm in height
Lipid bilayer membrane: formed by using a chloroform solution of a 1:1 (weight ratio) mixture of 1,2-dioleoyl-sn-glycero-3-phosphoethanolamine (DOPE) and 1,2-dioleoyl-sn-glycero-3-phosphoglycerol (DOPG)
Test liquid: an aqueous solution containing a 10 mM pH buffer (pH: 5 to 9), a 20 µM fluorescent membrane potential indicator (DiBac4) and a 10 mM sodium chloride
Voltage-applying apparatus: a function generator (manufactured by NF Corp.)
Confocal laser microscope: A1R (manufactured by Nikon Corp.)
The fluorescent membrane potential indicator: DiBAC4 (manufactured by Dojindo Laboratories); here, DiBAC4 is a bis-oxonol-type anionic membrane potential-susceptible pigment, and the distribution thereof in cytoplasms increases along with the depolarization of cell membranes and the fluorescence is enhanced.

Figure 10:
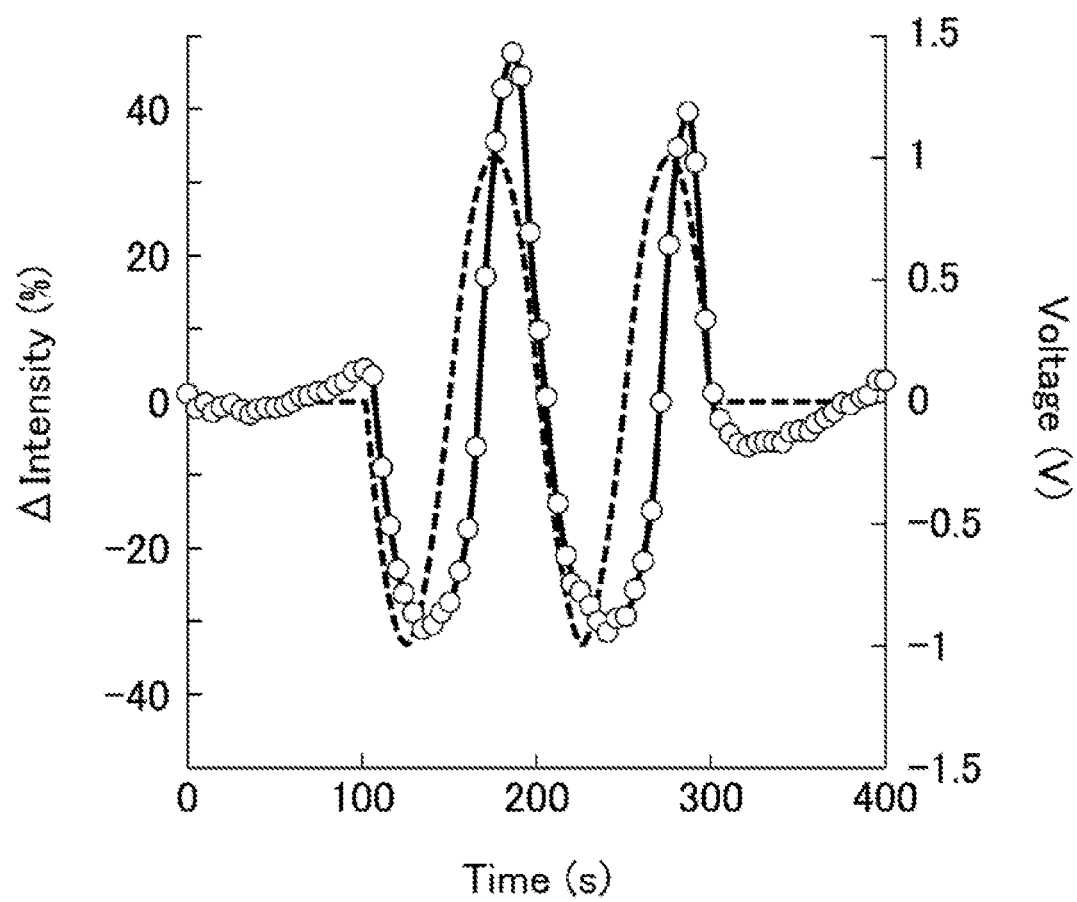
FIG. 10 is a diagram showing changes in the applied voltage (dashed line) and the fluorescent intensity (solid line) in a first Experimental Example.

FIG. 10 is a diagram showing changes in the applied voltage (dashed line) and the fluorescent intensity (solid line) in the first Experimental Example. The applied voltage was indicated by a potential of the counter electrode 27 on the basis (0 V) of the electrode 23 (the same was applied to the other Experimental Example). As shown in FIG. 10, the fluorescent intensity of DiBAC4 changed in such a way as to follow the applied voltage. It is clear that the change in the fluorescent intensity lagged a little behind the change in the applied voltage. From the result of the present Experimental Example, it is clear that when the high-density micro-chamber array of the first embodiment was used, the membrane potential (depolarized and hyperpolarized) could be controlled by the application of a voltage to the electrode.

2. Second Experimental Example

In a second Experimental Example, in the same high-density micro-chamber array 20A (see FIGS. 1, 2 and 3) as in the first Experimental Example, an F-type ATP synthase (FoF1) derived from *Bacillus coli* as the membrane protein was introduced to the lipid bilayer membrane 30 by using a liposome; and the active transport of protons was detected.

As the test liquid inside the micro-chamber 26, there was used an aqueous solution whose composition contained a 10 µM Tricine buffer (pH 8), a 10 mM sodium chloride (NaCl), a 10 mM calcium chloride ($CaCl_2$), a 2 mM magnesium chloride ($MgCl_2$), a 1 µM adenosine diphosphate (ADP) and a 20 µM fluorescent pH indicator (RhP-M).

As the liquid outside the micro-chamber 26, there was used an aqueous solution containing a 10 µM MOPS (3-morpholinopropanesulfonic acid) buffer (pH 8), a 10 mM sodium chloride (NaCl), a 10 mM calcium chloride ($CaCl_2$), a 2 mM magnesium chloride ($MgCl_2$) and a 240 µM adenosine triphosphate (ATP).

Since the other apparatus configuration was the same as in the first Experimental Example, detailed descriptions thereof will be omitted.

Figure 11:
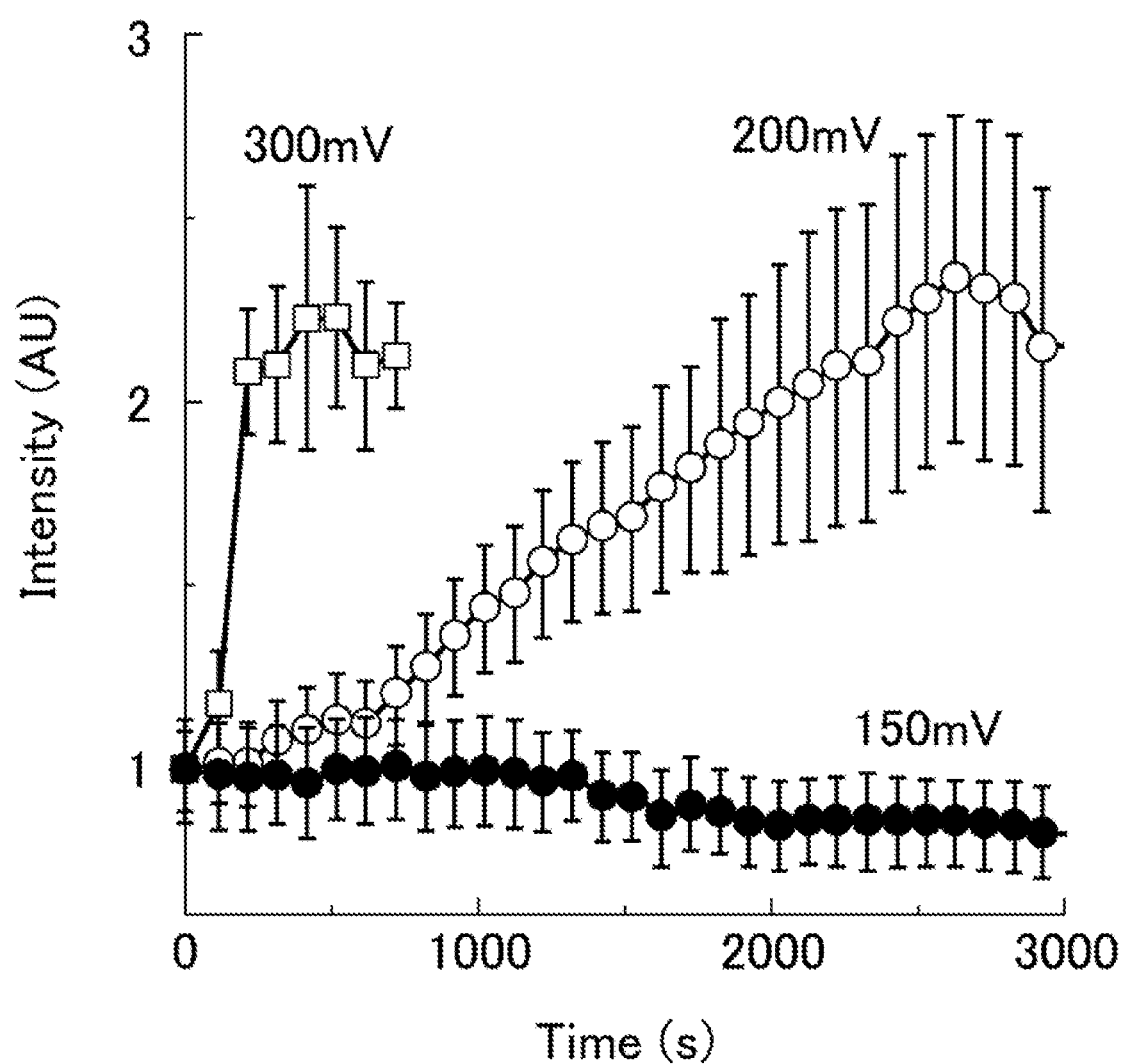
FIG. 11 is a diagram showing relations between the change with time in the fluorescent intensity and the membrane potentials in a second Experimental Example.
Figure 12:
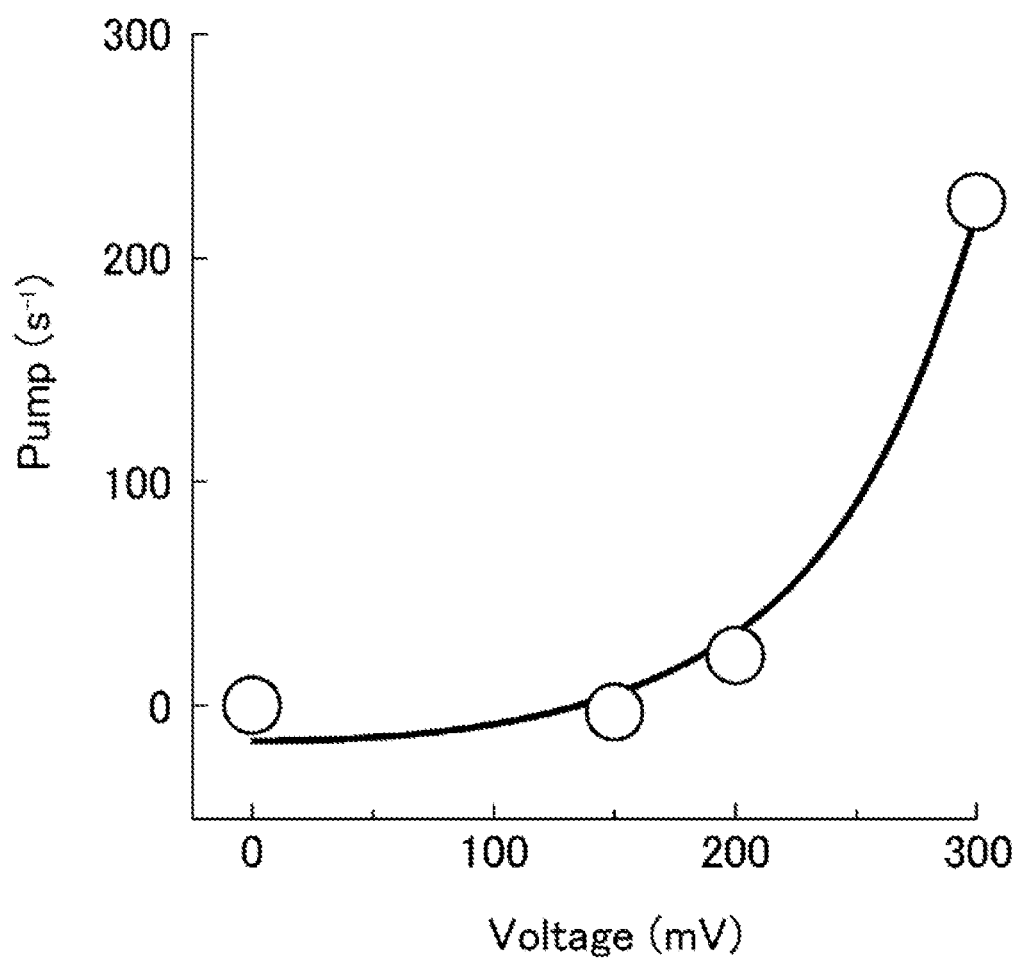
FIG. 12 is a diagram showing a relation between the proton transport rate (axis of ordinate) of an F-type ATP synthase and the magnitude of the membrane potential (axis of abscissa) in the second Experimental Example.

FIG. 11 is a diagram showing relations between the change with time in the fluorescent intensity and the membrane potentials in the second Experimental Example. FIG. 12 is a diagram showing a relation between the proton transport rate (axis of ordinate) of an F-type ATP synthase and the magnitude of the membrane potential (axis of abscissa) in the second Experimental Example.

As shown in FIG. 11, it is clear that a higher membrane potential gave a faster change in the fluorescent intensity and a higher proton transport rate.

Second Embodiment

In a second embodiment, the interiors of the micro-chambers are heated by causing a current to flow through the electrode.

A high-density micro-chamber array according to the second embodiment is the high-density micro-chamber array according to the first embodiment; and the electrode is a metal and is provided on the inner side surface of each of the micro-chambers.

In the high-density micro-chamber array, the metal may be chromium.

A high-density micro-chamber array system according to the second embodiment has any one of the above high-density micro-chamber arrays, and a current-applying apparatus to cause a current to flow parallel to the substrate in the electrode to thereby cause the electrode to generate heat.

The high-density micro-chamber array system may further have a counter electrode provided above the lipid bilayer membrane, and a voltage-applying apparatus to apply a voltage between the electrode and the counter electrode.

A method according to the second embodiment involves providing any one of the above high-density micro-chamber arrays, and causing a current to flow through the electrode arrays to cause the electrode to generate heat to thereby control the temperature of a test liquid sealed in the micro-chamber.

[Apparatus Configuration]

Figure 13:
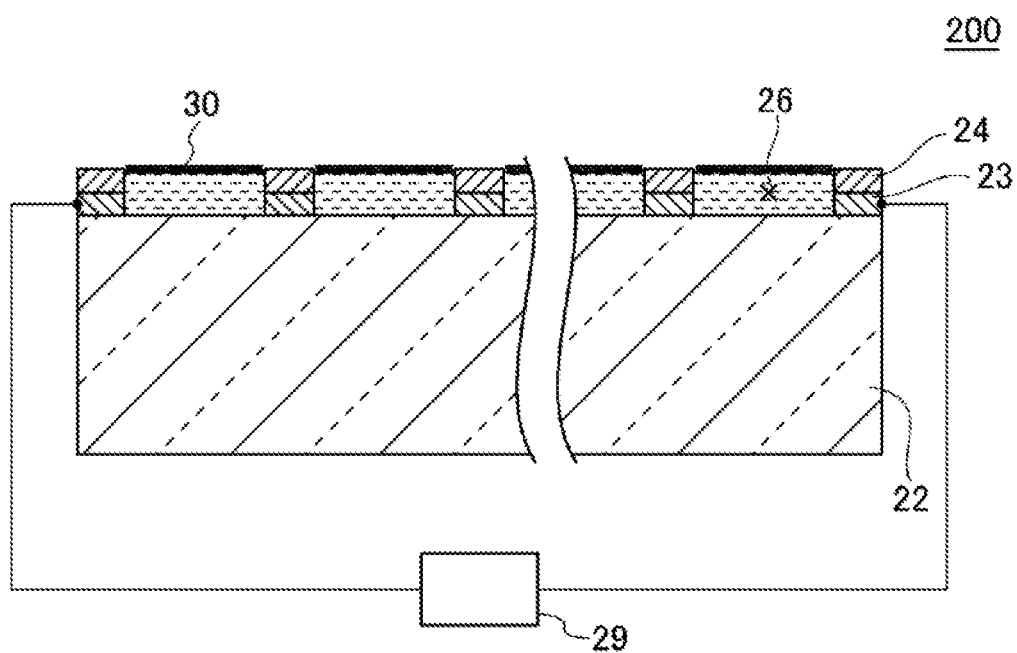
FIG. 13 is a view illustrating one example of a schematic configuration of a high-density micro-chamber array system according to a second embodiment.

FIG. 13 is a view illustrating one example of a schematic configuration of the high-density micro-chamber array system according to the second embodiment. Hereinafter, an apparatus configuration of a high-density micro-chamber array system 200 of the second embodiment will be described by reference to FIG. 13.

As illustrated in FIG. 13, the high-density micro-chamber array system 200 has a substrate 22, electrodes 23, a hydrophobic layer 24, micro-chambers 26, lipid bilayer membranes 30, and a current-applying apparatus 29.

Since the substrate 22, the hydrophobic layer 24, the micro-chambers 26 and the lipid bilayer membranes 30 can be configured similarly to the first embodiment, detailed descriptions thereof will be omitted.

The electrode 23 may be constituted of any material as long as being capable of being used as a heat-generating body. Specifically, the electrode 23 may be constituted of, for example, a metal. More specifically, the electrode 23 may be constituted of, for example, chromium.

Or, the electrode 23 may also be constituted of a material capable of being used as a heat-generating body and hardly susceptible to deterioration by a test liquid. Specifically, the electrode 23 may be constituted of chromium, for example.

In the example illustrated in FIG. 13, the corresponding electrodes 23 of the plurality of micro-chambers 26 are mutually electrically connected. That is, as in the hydrophobic layer 24 illustrated in FIG. 1, the electrode 23 may be continuously configured to surround the plurality of micro-chambers 26. In such a configuration, the plurality of micro-chambers 26 can be heated collectively.

The current-applying apparatus 29 causes a current to flow parallel to the substrate 22 in the electrode 23 to thereby cause the electrode 23 to generate heat. As the current-applying apparatus 29, specifically, for example, a function generator (manufactured by NF Corp.) can be used.

[Method]

In a method according to the second embodiment, by causing a current to flow through the electrode 23 by using the current-applying apparatus 29 to thereby cause the electrode 23 to generate heat, there can be controlled the temperature of the test liquid sealed in the micro-chamber 26, the lipid bilayer membrane 30, the membrane protein and the like.

By controlling the temperature of the test liquid sealed in the micro-chamber, the lipid bilayer membrane 30, the membrane protein and the like by using the electrode 23, the behavior of the membrane protein under more various conditions can be analyzed.

Also in the second embodiment, the same modification as in the first embodiment may be made. For example, the high-density micro-chamber array system 200 may have, in addition to the current-applying apparatus 29, a voltage-applying apparatus 28. Since the voltage-applying apparatus 28 can be configured similarly to the first embodiment, detailed descriptions thereof will be omitted.

Third Embodiment

In a third embodiment, a biopolymer is accumulated in the interiors of the micro-chambers sealed with the lipid bilayer membrane.

A high-density micro-chamber array according to the third embodiment is a high-density micro-chamber array according to at least one of the first embodiment and the second embodiment, and a biopolymer is accumulated in the interiors of the micro-chambers.

A method according to the third embodiment involves: providing a high-density micro-chamber array which has a translucent flat substrate, and a hydrophobic layer provided on the substrate and composed of a hydrophobic substance wherein on the principal surface of the hydrophobic layer, openings of a plurality of micro-chambers, each having a capacity of $4,000 \times 10^{-18}$ m$^3$ or smaller, are provided in such a way as to be arrayed regularly at a high density, wherein an electrode is provided in each of the micro-chambers, and when the side of the substrate on which the hydrophobic layer is provided is directed upward, the micro-chamber array is configured such that with at least one of the following A) and B) being met, light entering the substrate from below the substrate is transmitted through the substrate and penetrates into the interiors of the micro-chambers, and light entering the substrate from the interiors of the micro-chambers is transmitted through the substrate and escapes toward below the substrate; applying a voltage to the electrode to accumulate a biopolymer in the interiors of the plurality of micro-chambers; and thereafter forming lipid bilayer membranes in the openings of the plurality of micro-chambers in such a way as to seal the biopolymer.
A) The electrode is provided on an inner side surface of each of the micro-chambers.
B) The electrode is provided as a transparent electrode on a bottom surface of each of the micro-chambers.

[Apparatus Configuration]

Figure 14:
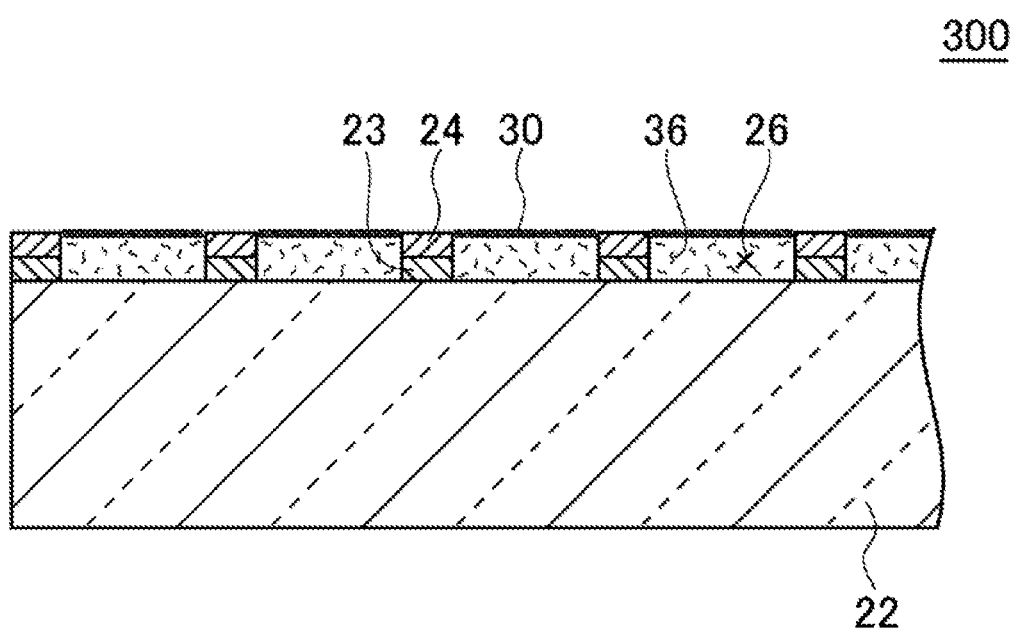
FIG. 14 is a view illustrating one example of a schematic configuration of a high-density micro-chamber array in which a biopolymer is accumulated in a third embodiment.

FIG. 14 is a view illustrating one example of a schematic configuration of a high-density micro-chamber array in which a biopolymer is accumulated in the third embodiment. Hereinafter, an apparatus configuration of a high-density micro-chamber array 300 of the third embodiment will be described by reference to FIG. 14.

As illustrated in FIG. 14, the high-density micro-chamber array 300 has a substrate 22, electrodes 23, a hydrophobic layer 24, micro-chambers 26 and lipid bilayer membranes 30.

Since the substrate 22, the electrode 23, the hydrophobic layer 24 and the lipid bilayer membranes 30 can be configured similarly to at least one of the first embodiment and the second embodiment, detailed descriptions thereof will be omitted.

Biopolymers 36 are accumulated in the interiors of the micro-chambers 26. The biopolymers include, for example, proteins, DNA and RNA.

[Manufacturing Method]

Hereinafter, a manufacturing method of the high-density micro-chamber array 300 of the third embodiment will be described. FIG. 15 is a process diagram showing one example of the method for producing the biopolymer-accumulated high-density micro-chamber array in the third embodiment.

The high-density micro-chamber array 300 of the third embodiment is completed by first forming a micro-chamber device in which each opening is not liquid-sealed with a lipid bilayer membrane 30 (step S400), introducing a test liquid to the formed micro-chamber device (step S410), accumulating biopolymers in each micro-chamber (step S420), and forming a lipid bilayer membrane 30 in such a way as to liquid-seal the opening of each of the micro-chambers 26 in such a state that the test liquid is filled in each of the micro-chambers 26 and the biopolymers are accumulated in each of the micro-chambers (step S430).

Since the step S400 can be carried out as in the step S100 of FIG. 5, detailed descriptions thereof will be omitted.

Since the step S410 can be carried out as in the step S110 of FIG. 5 or FIG. 9A, detailed descriptions thereof will be omitted.

Since the step S430 can be carried out as in the step S120 of FIG. 5 or FIGS. 9B and 9C, detailed descriptions thereof will be omitted.

In the step S420, the biopolymers 36 are induced in the interiors of the micro-chambers 26, for example, by using the electrode 23. The biopolymers 36 may have a charge. In this case, by charging the electrode 23 to an opposite polarity to the biopolymers 36, the biopolymers 36 can be induced to the micro-chambers 26.

The biopolymers 36 may be induced to the micro-chambers 26 by dielectric migration. In the dielectric migration, even if the biopolymers are electrically neutral particles, by applying a nonuniform electric field, the particles are polarized and can be caused to migrate. The dielectric migration is caused by the relation between dielectric constants of the liquid and the particles, and the spatial gradient of the electric field. In the case of using the dielectric migration, even in the case where the biopolymers 36 have no charge, the biopolymers 36 can be induced to the micro-chambers 26. In the present embodiment, since the electric field converges on the openings of the chambers, the substance can be induced into the chambers.

In the third embodiment, the biopolymers 36 can be accumulated in the interiors of the micro-chambers 26 sealed with the lipid bilayer membrane 30. Hence, the accumulation gives an advantage on the analysis of the interaction between the biopolymers 36, the interaction between the membrane protein held by the lipid bilayer membrane 30 and the biopolymers 36, and the like.

Fourth Embodiment

In a fourth embodiment, a membrane protein is introduced in the lipid bilayer membrane by cell fusion.

A method according to the fourth embodiment involves providing a high-density micro-chamber array according to at least one of the first embodiment to the third embodiment having a counter electrode, applying a current between the electrode and the counter electrode to cause cells to fuse to the lipid bilayer membranes to thereby cause a membrane protein derived from the cells to migrate to the lipid bilayer membranes.

The method of the fourth embodiment may comprise a step of providing a counter electrode above the lipid bilayer membranes in at least one method of the first embodiment to the third embodiment, wherein the membrane protein may be a membrane protein, derived from cells, which is introduced to the lipid bilayer membrane by applying a current between the electrode and the counter electrode to cause the cells to fuse to the lipid bilayer membrane.

Figure 16A:
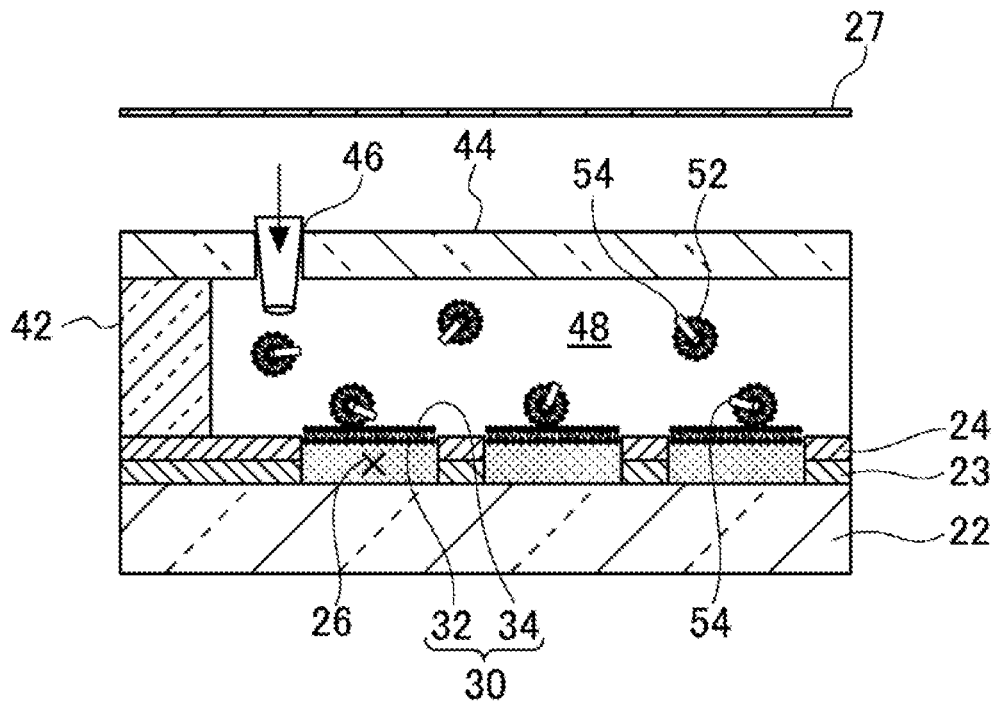
FIG. 16A is a view illustrating a step of introducing cells in a liquid channel in a method of causing the cells to fuse to lipid bilayer membranes according to a fourth embodiment.
Figure 16B:
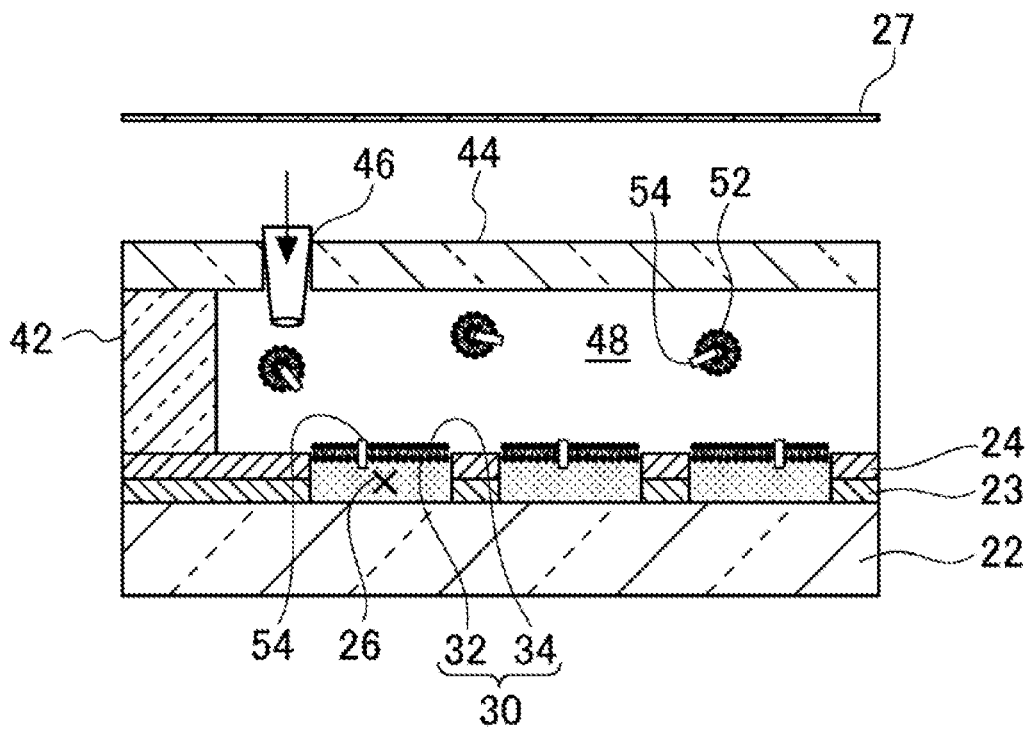
FIG. 16B is a view illustrating a state in which the cells have been caused to fuse to the lipid bilayer membranes in the method of causing the cells to fuse to the lipid bilayer membranes according to the fourth embodiment.

FIG. 16A is a view illustrating a step of introducing cells in a liquid channel in a method of causing the cells to fuse to the lipid bilayer membranes according to the fourth embodiment. FIG. 16B is a view illustrating a state that the cells are caused to fuse to the lipid bilayer membranes in the method of causing the cells to fuse to the lipid bilayer membranes according to the fourth embodiment. Hereinafter, by reference to FIGS. 16A and 16B, the method of the fourth embodiment will be described. Here, in FIGS. 16A and 16B, constituents in common with FIG. 3, since being capable of making the same configuration as that of the first embodiment, are given the same reference signs and names, and detailed descriptions thereof will be omitted.

The introduction of the membrane protein 54 in the lipid bilayer membrane 30 by using a cell fusion technology can be carried out, for example, as follows. That is, a glass plate 44 is mounted on a micro-chamber device through a spacer 42 to form the liquid channel 48. In this state, a solution containing the cells 52 having the membrane protein 54 is introduced from a liquid-introducing hole 46 of the glass plate 44 (FIG. 16A); by applying a pulsing direct current between the electrode 23 and the counter electrode 27 by using a current-applying apparatus 28 (not illustrated in the figure) to thereby incorporate the membrane protein 54 in the lipid bilayer membrane 30 by cell fusion (FIG. 16B). As the composition of the solution, there can be used a solution containing a 10 nM FoF1 (an ATP synthase), a 1 mM MOPS (3-morpholinopropane-1-sulfonic acid) of a pH of 7, a 10 mM sodium chloride (NaCl) and a 2 mM magnesium chloride ($MgCl_2$).

When the configuration is made such that the membrane protein 54 is reconstituted in the lipid bilayer membrane 30 of a high-density micro-chamber array according to any one of the first embodiment to the third embodiment, the high-density micro-chamber array can be used for the detection of biomolecular reactions and the like through the membrane protein. Since the membrane protein 54 can be introduced directly from the cells 52 to the lipid bilayer membrane 30, the operation can be simplified. Since the membrane protein 54 which the cells 52 have can be analyzed as it is, unknown membrane proteins which cells express are enabled to be analyzed.

In the cell fusion, the inside (cytoplasm side) and the outside (extracellular matrix side) of the lipid bilayer membrane are conserved. Hence, the orientation of the membrane protein 54 introduced in the lipid bilayer membrane 30 can suitably be controlled by utilizing the cell fusion. When cells are caused to fuse to the lipid bilayer membrane 30 from the outside of the micro-chamber 26, the interior of the micro-chamber 26 becomes the cytoplasm side. When cells are accumulated in the interior of the micro-chamber 26 and are caused to fuse to the lipid bilayer membrane 30 from the inside of the micro-chamber 26, the interior of the micro-chamber 26 becomes the extracellular matrix side.

From the above descriptions, improvements and other embodiments of the present invention are obvious for those skilled in the art. Therefore, the above descriptions should be interpreted just as exemplifications, and have been provided for the purpose of instructing those skilled in the art of the best mode to carry out the present invention. Details of the structure and/or the function can substantially be varied without departing from the spirit of the present invention.

REFERENCE SIGNS LIST

10 CAMERA
12 LASER LIGHT SOURCE
14 DICHROIC MIRROR
20 HIGH-DENSITY MICRO-CHAMBER ARRAY
22 SUBSTRATE
23 ELECTRODE
23a ELECTRODE LAYER
24 HYDROPHOBIC LAYER
24a SUBSTANCE MEMBRANE
24b SUBSTANCE MEMBRANE
25a RESIST
25b RESIST
26 MICRO-CHAMBER
27 COUNTER ELECTRODE
28 VOLTAGE-APPLYING APPARATUS
29 CURRENT-APPLYING APPARATUS
30 LIPID BILAYER MEMBRANE
32 FIRST LIPID MEMBRANE
34 SECOND LIPID MEMBRANE
35 LIPID
36 BIOPOLYMER
42 SPACER
44 GLASS PLATE
46 LIQUID-INTRODUCING HOLE
48 LIQUID CHANNEL
52 CELL
54 MEMBRANE PROTEIN
100 HIGH-DENSITY MICRO-CHAMBER ARRAY SYSTEM
200 HIGH-DENSITY MICRO-CHAMBER ARRAY SYSTEM
300 HIGH-DENSITY MICRO-CHAMBER ARRAY

The invention claimed is:

1. A high-density micro-chamber array, comprising:
a translucent flat substrate;
a hydrophobic layer provided on the translucent flat substrate and composed of a hydrophobic substance wherein on a principal surface of the hydrophobic layer, openings of a plurality of micro-chambers, each having a capacity of $4,000 \times 10^{-18}$ $m^3$ or smaller, are provided in such a way as to be arrayed regularly at a high density; and
a plurality of individual lipid bilayer membranes, each formed in such a way as to seal a test liquid within each of the plurality of micro-chambers by being located in each of the openings of the plurality of micro-chambers in a state of being filled with the test liquid,
wherein
a top surface of the hydrophobic layer is so exposed that the plurality of individual lipid bilayer membranes are separated from one another;
an electrode is provided in each of the micro-chambers;
when a side of the translucent flat substrate having the hydrophobic layer provided on the side is directed upward, the micro-chamber array is configured such that with at least one of the following A) and B) being met, light entering the translucent flat substrate from below the translucent flat substrate is transmitted through the translucent flat substrate and penetrates into interiors of the micro-chambers, and light entering the translucent flat substrate from the interiors of the micro-chambers is transmitted through the translucent flat substrate and escapes toward below the translucent flat substrate:
A) the electrode is provided on an inner side surface of each of the micro-chambers; and
B) the electrode is provided as a transparent electrode on a bottom surface of each of the micro-chambers; and
a counter electrode is provided above the plurality of individual lipid bilayer membranes.

2. The high-density micro-chamber array according to claim 1, wherein in an interior of the micro-chamber, a biopolymer is accumulated.

3. The high-density micro-chamber array according to claim 1, comprising a liquid channel having a bottom surface thereof formed by a surface on which the micro-chamber is formed.

4. A high-density micro-chamber array system, comprising:
the high-density micro-chamber array according to claim 1; and a voltage-applying apparatus to apply a voltage between the electrode and the counter electrode.

5. A high-density micro-chamber array system, comprising:
the high-density micro-chamber array according to claim 1, wherein the electrode is a metal, and is provided on an inner side surface of each of the micro-chambers; and
a current-applying apparatus to cause a current to flow through the electrode parallel to the translucent flat substrate to thereby cause the electrode to generate heat.

6. The high-density micro-chamber array system according to claim 5, further comprising:
a voltage-applying apparatus to apply a voltage between the electrode and the counter electrode.

7. A method, comprising:
providing the high-density micro-chamber array according to claim 5; and
causing a current to flow through the electrode to cause the electrode to generate heat to thereby control a temperature of the test liquid sealed in the micro-chamber.

8. A method, comprising:
providing the high-density micro-chamber array according to claim 1; and
applying a current between the electrode and the counter electrode to cause a cell to fuse to the lipid bilayer membrane to thereby cause a membrane protein derived from the cell to migrate to the lipid bilayer membrane.

9. A method for analyzing a membrane protein, comprising:
providing a high-density micro-chamber array comprising a translucent flat substrate and a hydrophobic layer provided on the translucent flat substrate and composed of a hydrophobic substance wherein on a principal surface of the hydrophobic layer, openings of a plurality of micro-chambers, each having a capacity of $4,000 \times 10^{-18}$ m$^3$ or smaller, are provided in such a way as to be arrayed regularly at a high density, wherein an electrode is provided in each of the micro-chambers, and when a side of the translucent flat substrate having the hydrophobic layer provided on the side is directed upward, the micro-chamber array is configured such that with at least one of the following A) and B) being met, light entering the translucent flat substrate from below the translucent flat substrate is transmitted through the translucent flat substrate and penetrates into interiors of the micro-chambers, and light entering the translucent flat substrate from the interiors of the micro-chambers is transmitted through the translucent flat substrate and escapes toward below the translucent flat substrate;
forming a lipid bilayer membrane in each of the openings of the plurality of micro-chambers in such a way as to leave a top surface of the hydrophobic layer exposed, wherein the lipid bilayer membrane is to hold a membrane protein; and
applying a voltage between the electrode and a counter electrode provided above the lipid bilayer membrane to thereby change properties of the membrane protein:
A) the electrode is provided on an inner side surface of each of the micro-chambers; and
B) the electrode is provided as a transparent electrode on a bottom surface of each of the micro-chambers.

10. The method for analyzing a membrane protein according to claim 9,
wherein the step of providing the high-density micro-chamber array comprises a step of providing the counter electrode above the lipid bilayer membrane; and
wherein the membrane protein is a membrane protein derived from a cell, the membrane protein being introduced to the lipid bilayer membrane by applying a current between the electrode and the counter electrode to thereby cause the cell to fuse to the lipid bilayer membrane.

11. A method, comprising:
providing a high-density micro-chamber array comprising a translucent flat substrate, and a hydrophobic layer provided on the translucent flat substrate and composed of a hydrophobic substance wherein on a principal surface of the hydrophobic layer, openings of a plurality of micro-chambers, each having a capacity of $4,000 \times 10^{-18}$ m$^3$ or smaller, are provided in such a way as to be arrayed regularly at a high density, wherein an electrode is provided in each of the micro-chambers, and when a side of the translucent flat substrate having the hydrophobic layer provided on the side is directed upward, the micro-chamber array is configured such that with at least one of the following A) and B) being met, light entering the translucent flat substrate from below the translucent flat substrate is transmitted through the translucent flat substrate and penetrates into interiors of the micro-chambers, and light entering the translucent flat substrate from the interiors of the micro-chambers is transmitted through the translucent flat substrate and escapes toward below the translucent flat substrate;
applying a voltage to the electrode to accumulate a biopolymer in interiors of the plurality of micro-chambers; and
thereafter forming a lipid bilayer membrane in each of the openings of the plurality of micro-chambers in such a way as to seal the biopolymer and to leave a top surface of the hydrophobic layer exposed:
A) the electrode is provided on an inner side surface of each of the micro-chambers; and
B) the electrode is provided as a transparent electrode on a bottom surface of each of the micro-chambers.

* * * * *